United States Patent
Blanchard et al.

(10) Patent No.: US 9,938,324 B2
(45) Date of Patent: Apr. 10, 2018

(54) FRET-BASED REAGENTS AND METHODS FOR IDENTIFYING ANTI-HIV COMPOUNDS

(71) Applicants: Cornell University, Ithaca, NY (US); YALE UNIVERSITY, New Haven, CT (US)

(72) Inventors: Scott C. Blanchard, New York, NY (US); Walther Mothes, Middletown, CT (US); James Munro, New Haven, CT (US)

(73) Assignees: CORNELL UNIVERSITY, Ithaca, NY (US); YALE UNIVERSITY, New Haven, CT (US)

(*) Notice: Subject to any disclaimer, the term of this patent is extended or adjusted under 35 U.S.C. 154(b) by 69 days.

(21) Appl. No.: 14/402,709

(22) PCT Filed: May 22, 2013

(86) PCT No.: PCT/US2013/042249
§ 371 (c)(1),
(2) Date: Nov. 21, 2014

(87) PCT Pub. No.: WO2013/177294
PCT Pub. Date: Nov. 28, 2013

(65) Prior Publication Data
US 2015/0166611 A1 Jun. 18, 2015

Related U.S. Application Data

(60) Provisional application No. 61/650,180, filed on May 22, 2012.

(51) Int. Cl.
C07K 14/005 (2006.01)
C12N 7/00 (2006.01)
G01N 33/542 (2006.01)
G01N 33/569 (2006.01)
G01N 33/58 (2006.01)

(52) U.S. Cl.
CPC .............. *C07K 14/005* (2013.01); *C12N 7/00* (2013.01); *G01N 33/542* (2013.01); *G01N 33/56988* (2013.01); *G01N 33/582* (2013.01); *C12N 2740/15022* (2013.01); *C12N 2740/16122* (2013.01); *G01N 2500/00* (2013.01); *G01N 2500/04* (2013.01)

(58) Field of Classification Search
None
See application file for complete search history.

(56) References Cited

U.S. PATENT DOCUMENTS 7,141,655 B2  11/2006  Ebright et al.

FOREIGN PATENT DOCUMENTS

WO  2005/020889 A2  3/2005
WO  2010/096720 A2  8/2010
WO  2011/143575 A2  11/2011
WO  2012/003234 A2  1/2012

OTHER PUBLICATIONS

Laird et al., Journal of Virology, 2007, 81(20):10838-10848.*
Endrich et al., Eur. J. Biochem., 1998, 252:441-446.*
Liang et al., Vaccine, 1999, 17:2862-2872.*
Xiang, S.H. et al., "A V3 Loop-Dependent gp120 Element Disrupted by CD4 Binding Stabilizes the Human Immunodeficiency Virus Envelope Glycoprotein Trimer" J Virol (Apr. 2010) pp. 3147-3161, vol. 84, No. 7.
Zhou, Z. et al., "Genetically Encoded Short Peptide Tags for Orthogonal Protein Labeling by Sfp and AcpS Phosphopantetheinyl Transferases" ACS Chem Biol (2007) pp. 337-346, vol. 2, No. 5.
International Search Report dated Sep. 5, 2013 issued in International Application No. PCT/US2013/042249.
Altman, R.B. et al., "Enhanced photostability of cyanine fluorophores across the visible spectrum" Nat Methods (May 2012) pp. 428-429, vol. 9, No. 5.
Bastian, A.R. et al., "Cell-Free HIV-1 Virucidal Action by Modified Peptide Triazole Inhibitors of Env gp120" ChemMedChem (2011) pp. 1335-1339, vol. 6.
Beddows, S. et al., "Construction and Characterization of Soluble, Cleaved, and Stabilized Trimeric Env Proteins Based on HIV Type 1 Env Subtype A" AIDS Res Hum Retroviruses (2006) pp. 569-579, vol. 22, No. 6.
Beddow, S. et al., "A comparative immunogenicity study in rabbits of disulfide-stabilized, proteolytically cleaved, soluble trimeric human immunodeficiency virus type 1 gp140, trimeric cleavage-defective gp140 and monomeric gp120" Virology (2007) pp. 329-340, vol. 360.
Chen, B. et al., "Determining the Structure of an Unliganded and Fully Glycosylated SIV gp120 Envelope Glycoprotein" Structure (2005) pp. 197-211, vol. 13, No. 2.
Dave, R. et al., "Mitigating Unwanted Photophysical Processes for Improved Single-Molecule Fluorescence Imaging" Biophys J (Mar. 2009) pp. 2371-2381, vol. 96, No. 6.
Fu, N. et al., "Synthesis of a Targeted Biarsenical Cy3-Cy5 Affinity Probe for Superresolution Fluorescence Imaging" J. Am. Chem. Soc. (2012) pp. 18530-18533, vol. 134.
Gopi, H. et al., "Introducing metallocene into a triazole peptide conjugate reduces its off-rate and enhances its affinity and antiviral potency for HIV-1 gp120" J Mol Recognit (2009) pp. 167-174, vol. 22.

(Continued)

*Primary Examiner* — Nicole Kinsey White
(74) *Attorney, Agent, or Firm* — Scully Scott Murphy & Presser

(57) ABSTRACT

A modified HIV gp120 protein labeled with a fluorophore has been used herein in single-molecule imaging techniques to demonstrate the conformation states of HIV-1 Env. The introduction of small organic fluorophores at selected positions within HIV-1 envelope protein gp120 that do not affect infectivity permits the detection of changes in inter-dye distances as a measure of conformational changes. Implementation of the smFRET-based technologies disclosed herein enable conformational screening for molecules that block, induce or trap HIV-1 Env in specific conformational states. Methods for identifying anti-HIV drugs in a smFRET-based screening, and various reagents useful for implementation of such methods, are provided.

Figures 1A, 1B, 1C:
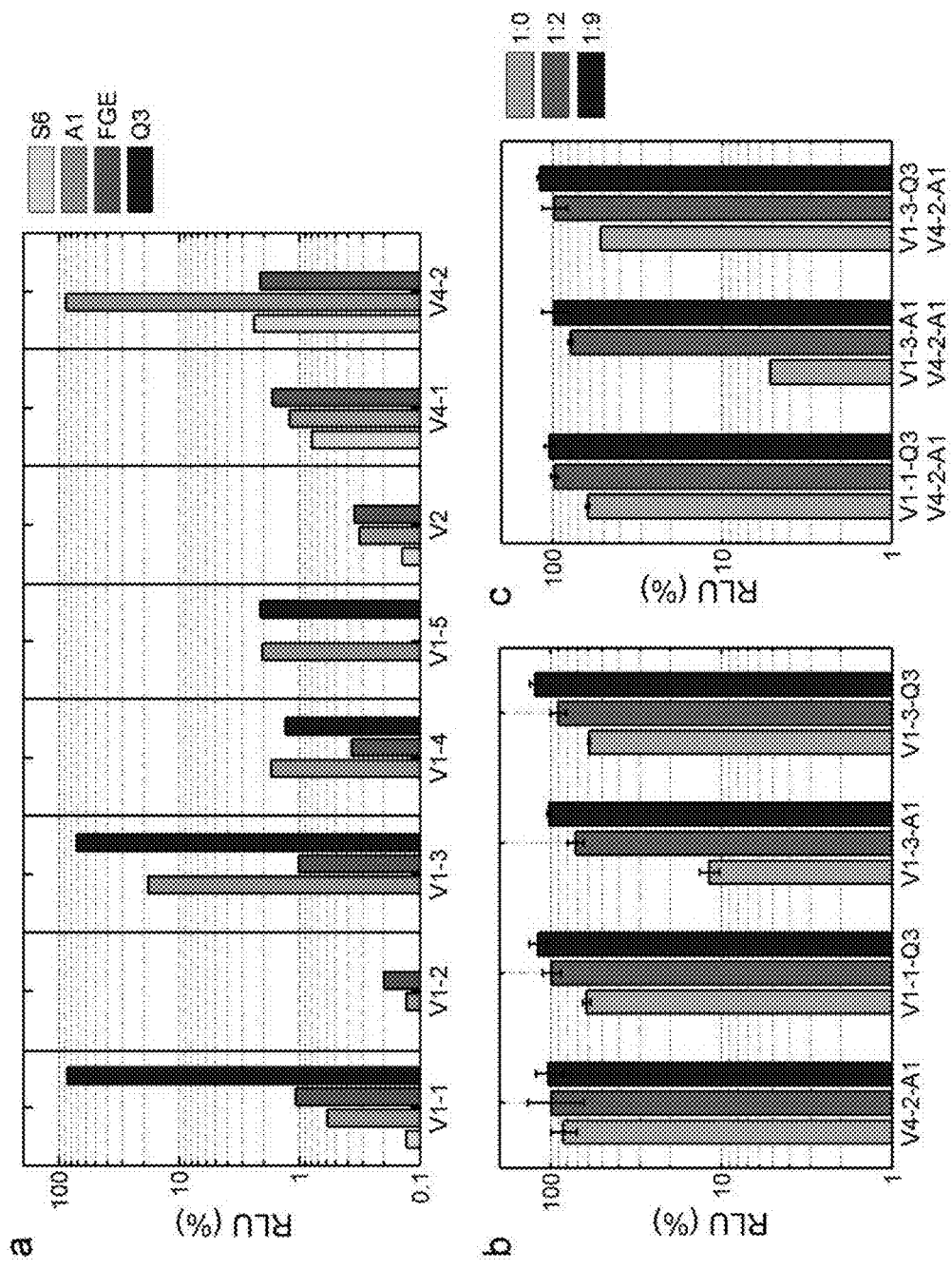

22 Claims, 15 Drawing Sheets
(12 of 15 Drawing Sheet(s) Filed in Color)

(56) References Cited

OTHER PUBLICATIONS

Griffin, B.A. et al., "Specific Covalent Labeling of Recombinant Protein Molecules Inside Live Cells" Science (1998) pp. 269-272, vol. 281.
Guttman, M. et al., "Solution Structure, Conformational Dynamicsm and CD4-Induced Activation in Full-Length, Glycoylated, Monomeric HIV gp120" J Virol (2012) pp. 8750-8764, vol. 86, No. 16.
Haim, H. et al., "Soluble CD4 and CD4-Mimetic Compounds Inhibit HIV-1 Infection by Induction of a Short-Lived Activated State" PLoS Pathog (Apr. 2009) pp. 1-13, vol. 5, No. 4, e1000360.
Harris, A. et al., "Trimeric HIV-1 glycoprotein gp140 immunogens and native HIV-1 envelope glycoproteins display the same closed and open quaternary molecular architectures" Proc Natl Acad Sci USA (Jul. 2011) pp. 11440-11445, vol. 108, No. 28.
Henzler-Wildman, K. et al., "Dynamic Personalitied of Proteins" Nature (Dec. 2007) pp. 964-972, vol. 450, No. 7172.
Hu, G. et al., "Structural Comparison of HIV-1 Envelope Spikes with and without the V1/V2 Loop" J Virol (Mar. 2011) pp. 2741-2750, vol. 85, No. 6.
Huang, C.C. et al., "Structures of the CCR5 N Terminus and of a Tyrosine-Sulfated Antibody with HIV-1 gp120 and CD4" Science (2007) pp. 1930-1934, vol. 317.
Huang, C.C. et al., "Structure of a V3-Containing HIV-1 gp120 Core" Science (2005) pp. 1025-1028, vol. 310.
Kwon, Y.D. et al., "Unliganded HIV-1 gp120 core structures assume the CD4-bound conformation with regulation by quaternary interactions and variable loops" Proc Natl Acad Sci USA (Apr. 2012) pp. 5663-5668, vol. 109, No. 15.
Kwong, P.D. et al., "Structure of an HIV gp120 enevelope glycoprotein in complex with with CD4 receptor and a neutralizing human antibody" Nature (Jun. 1998) pp. 648-659, vol. 393, No. 6686.
Laird, M.E. et al., "Infectivity and Neutralization of Simian Immunodeficiency Virus with FLAG Epitope Insertion in gp120 Variable Loops" J Virol (Oct. 2007) pp. 10838-10848, vol. 81, No. 20.
Leung, K. et al., "HIV-1 Assembly: Viral Glycoproteins Segregate Quantally to Lipid Rafts that Associate Individually with HIV-1 Capsids and Virions" Cell Host Microbe (May 2008) pp. 285-292, vol. 3.
Lin, C.W. et al., "Transglutaminase-catalyzed site-specific conjugation of small-molecule probes to proteins in vitro and on the surface of living cells" J Am Chem Soc (Apr. 2006) pp. 4542-4543, vol. 128, No. 14.
Liu, J. et al., "Molecular architecture of native HIV-1 gp120 trimers" Nature (Sep. 2008) pp. 109-113, vol. 455, No. 7209.
Madani, N. et al., "Small-Molecule CD4 Mimics Interact with a Highly Conserved Pocket on HIV-1 gp120" Structure (Nov. 2008) pp. 1689-1701, vol. 16.
Mazurov, D. et al., "Quantitative Comparison of HTLV-1 and HIV-1 Cell-to-Cell Infection with New Replication Dependent Vectors" PLoS Pathog (Feb. 2010) pp. 1-11, vol. 6, No. 2, e1000788.
McFadden, K. et al., "Antiviral Breadth and Combination Potential of Peptide Triazole HIV-1 Entry Inhibitors" Antimicrob Agents Chemother (2012) pp. 1073-1080, vol. 56.
McKinney, S.A. et al., "Analysis of Single-Molecule FRET Trajectories Using Hidden Markov Modeling" Biophys J (Sep. 2006) pp. 1941-1951, vol. 91, No. 5.
McLellan, J.S. et al., "Structure of HIV-1 gp120 V1/V2 domain with broadly neutralizing antibody PG9" Nature (Dec. 2011) pp. 336-343, vol. 480, No. 7377.
Mukherjee, N.G. et al., "Rapid modification of retroviruses using lipid conjugates" Nanotechnology (2009) pp. 1-10, vol. 20, No. 6: 065103.
Munro, J.B. et al., "Correlated Conformational events in EF-G and the ribosome regulate translocation" Nat Struct Mol Biol (Dec. 2010) pp. 1470-1477, vol. 17, No. 2.

Munro, J.B. et al., "Identification of Two Distinct Hybrid State Intermediates on the Ribosome" Mol Cell (Feb. 2007) pp. 505-517, vol. 25.
Munro, J.B. et al., "Navigating the ribosome's metastable energy landscape" Trends Biochem Sci (2009) pp. 390-400, vol. 34, No. 8.
Munro, J.B. et al., "A fast dynamic mode of the EF-G-bound ribosome" EMBO J. (2010) pp. 770-781, vol. 29, No. 4.
Nwe, K. et al., "Growing Applications of "Click Chemistry" for Bioconjugation in Contemporary Biomedical Research" Cancer Biother. Radiopharm. (2009) pp. 289-302, vol. 24, No. 3.
Olshevsky, U. et al., "Identification of Individual Human Immunodeficiency Virus Type I gp120 Amino Acids Important for CD4 Receptor Binding" J Virol (Dec. 1990) pp. 5701-5707, vol. 64, No. 12.
Pancera, M. et al., "Structure of HIV-1 gp120 with gp41-interactive region reveals layered envelope architecture and basis of conformational mobility" Proc Natl Acad Sci USA (Jan. 2010) pp. 1166-1171, vol. 107, No. 3.
Qin, F. et al., "Estimating Single-Channel Kinetic Parameters from Idealized Patch-Clamp Data Containing Missing Events" Biophys J (Jan. 1996) pp. 264-280, vol. 70.
Qin, F., "Restoration of Single-Channel Currents Using the Segmental k-Means Method Based on Hidden Markov Modeling" Biophys J (Mar. 2004) pp. 1488-1501, vol. 86, No. 3.
Rabuka, D. et al., "Site-specific chemical protein conjugation using genetically encoded aldehyde tags" Nat Prot (2012) pp. 1052-1067, vol. 7, No. 6.
Ren, X. et al., "An unrelated monoclonal antibody neutralizes human immunodeficiency virus type 1 by binding to an artificial epitope engineered in a functionally neutral region of the viral envelope glycoproteins" J Virol (May 2005) pp. 5616-5624, vol. 79, No. 9.
Roy, R. et al., "A practical guide to single-molecule FRET" Nat Methods (Jun. 2008) pp. 507-516, vol. 5, No. 6.
Rusert, P. et al., "Interaction of the gp120 V1V2 loop with a neighboring gp120 unit shields the HIV envelope trimer against cross-neutralizing antibodies" J Exp Med (2011) pp. 1419-1433, vol. 208, No. 7.
Sanders, R. et al., "Stabilization of the soluble, cleaved, trimeric form of the envelope glycoprotein complex of the human immunodeficiency virus type 1" J Virol (Sep. 2002) pp. 8875-8889, vol. 76, No. 17.
Schön, A. et al., "Thermodynamics of Binding of a Low-Molecular-Weight CD4 Mimetic to HIV-1 gp120" Biochemistry (2006) pp. 10973-10980, vol. 45.
Skilling, J. et al., "Maximum entroy image reconstruction: general algorithm" Mon Not R Astr Soc (1984) pp. 111-124, vol. 211.
Sullivan, N. et al., "CD4-induced confirmational changes in the human immuodeficiency virus type 1 gp120 glycoprotein: consequences for virus entry and neutralization" J Virol (Jun. 1998) pp. 4694-4703, vol. 72, No. 6.
Tran, E. et al., "Structural Mechanism of Trimeric HIV-1 Envelope Glycoprotein Activation" PLoS Pathog (Jul. 2012) pp. 1-18, vol. 8, No. 7, e1002797.
Walker, L.M. et al., "Broad neutralization coverafe ofg HIV by multiple highly potent antibodies" Nature (Sep. 2011) pp. 466-470, vol. 477.
Walker, L.M. et al., "Broad and Potent Neutralizing Antibodies from an African Donor Receal a New HIV-1 Vaccine Target" Science (2009) pp. 285-289, vol. 326.
White, T.A. et al., "Molecular Architectures of Trimeric SIV and HIV-1 Envelope Glycoproteins on Intact Viruses: Strain-Dependent Variation in Quaternary Structure" PLoS Pathog (Dec. 2010) pp. 1-14, vol. 6, No. 2, e1001249.
Wu, P. et al., "Site-specific chemical modification of recombinant proteins produced in mamalian cells by using the genetically encoded aldehyde tag" Proc Natl Acad Sci USA (Mar. 2009) pp. 3000-3005, vol. 106, No. 9.

* cited by examiner

|        |     |                                                                              | SEQ ID NO: |
|--------|-----|------------------------------------------------------------------------------|------------|
| NL43       | 80  | VKLTPLCVSLKCTDLKNDTNTNSSS-G------RM-I----MEK----GEIKNCSFN                    | 11 |
| NL43_V1-1-Q3 |   | VKLTPLCVSLKCTDLKNDTNTNSSS-GQQQLG-RM-I----MEK----GEIKNCSFN                    | 12 |
| JRFL       |     | VKLTPLCVTLNCKDV-NATNTNDSEG------T-------MER----GEIKNCSFN                     | 13 |
| KNH1144    |     | VKLTPLCVTLNCTDV------TNVTDVS-G------TRGNITI-M-KEMEGEIKNCSFN                  | 14 |
| BG505      |     | VKLTPLCVTLQCTNV------TNN-------------ITDDM-R----GEIKNCSFN                    | 15 |
|            |     |                                                                              |    |
| NL43       | 80  | VKLTPLCVSLKCTDLKND------TNT-NSSSG-RM-I----MEK----GEIKNCSFN                   | 11 |
| NL43_V1-2-Q3 |   | VKLTPLCVSLKCTDLKNGQQQLGTNT-NSSSG-RM-I----MEK----GEIKNCSFN                    | 16 |
| JRFL       |     | VKLTPLCVTLNCKDV-NA------TNTTNDSEGT------MER----GEIKNCSFN                     | 13 |
| KNH1144    |     | VKLTPLCVTLNCTDV---------TNVTDVS-GTRGNITI-M-KEMEGEIKNCSFN                     | 14 |
| BG505      |     | VKLTPLCVTLQCTNV---------TNN-------------ITDDM-R----GEIKNCSFN                 | 15 |
|            |     |                                                                              |    |
| NL43       | 80  | VKLTPLCVSLKCTDLKND------TNT-NSSSG-RM-I----MEK----GEIKNCSFN                   | 11 |
| NL43_V1-2-A1 |   | VKLTPLCVSLKCTDLKNGDSLDMLEWSLMTNT-NSSSG-RM-I----MEK----GEIKNCSFN              | 17 |
| JRFL       |     | VKLTPLCVTLNCKDV-NA------TNTTNDSEGT------MER----GEIKNCSFN                     | 13 |
| KNH1144    |     | VKLTPLCVTLNCTDV---------TNVTDVS-GTRGNITI-M-KEMEGEIKNCSFN                     | 14 |
| BG505      |     | VKLTPLCVTLQCTNV---------TNN-------------ITDDM-R----GEIKNCSFN                 | 15 |
|            |     |                                                                              |    |
| NL43       | 369 | TW-------------STEGSNNTEG                                                    | 18 |
| NL43_V4-2-A1 |   | TW--GDSLDMLEWSLMSTEGSNNTEG                                                   | 19 |
| JRFL       |     | TWNNN------------TEGSNNTEG                                                   | 20 |
| KNH1144    |     | TWN----------TSMSGSSNTET                                                     | 21 |
| BG505      |     | T------------SVQGSNST-G                                                      | 22 |

Figure 4

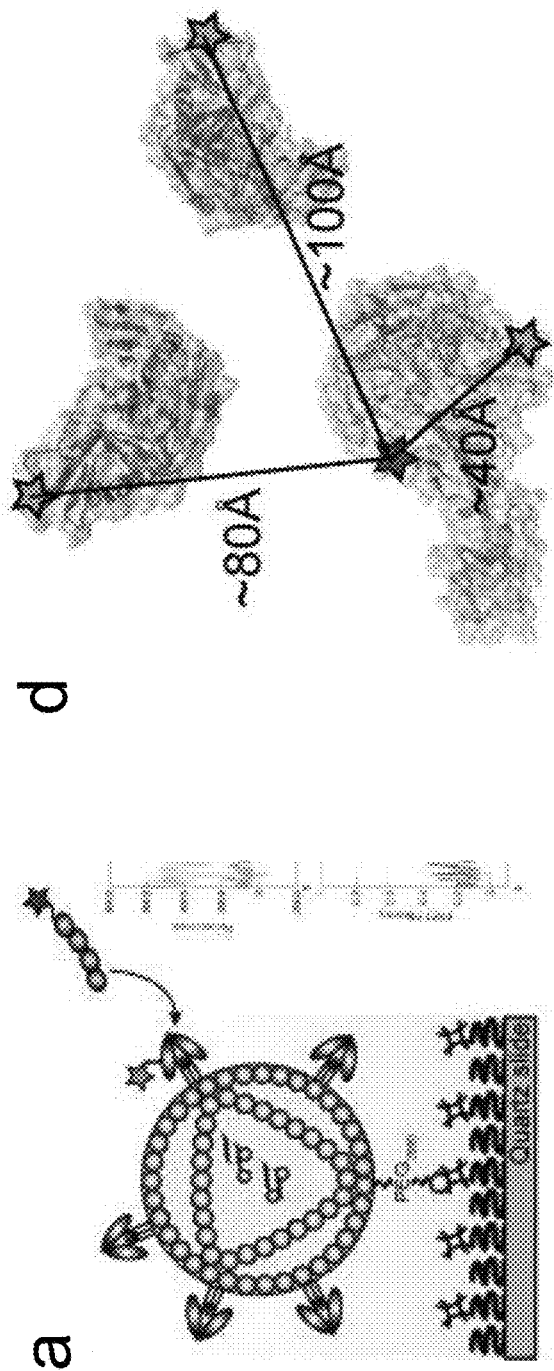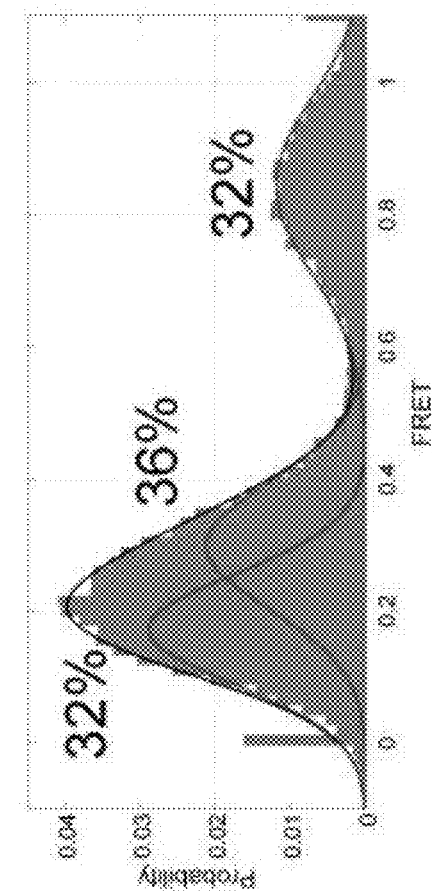
Figures 9a, 9c-9d

– 1 –

SEQUENCE LISTING

<160> NUMBER OF SEQ ID NOS: 22

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 1

Gly Asp Ser Leu Ser Trp Leu Leu Arg Leu Leu Asn
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 2

Gly Asp Ser Leu Asp Met Leu Glu Trp Ser Leu Met
1               5                   10

<210> SEQ ID NO 3
<211> LENGTH: 6
<212> TYPE: PRT

```
<213> ORGANISM: Artificial Sequence
<220> FEATURE:
<223> OTHER INFORMATION: Synthetic Peptide

<400> SEQUENCE: 3

Gly Gln Gln Gln Leu Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 4

Leu Cys Xaa Pro Xaa Arg
1               5

<210> SEQ ID NO 5
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 5

Cys Thr Asp Leu Lys Asn Gly Gln Gln Gln Leu Gly Thr Asn Thr Asn
1               5                   10                  15

Ser Ser Ser Gly
            20

<210> SEQ ID NO 6
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 6

Cys Thr Asp Leu Lys Asn Gly Asp Ser Leu Asp Met Leu Glu Trp Ser
1               5                   10                  15

Leu Met Thr Asn Thr Asn Ser Ser Ser Gly
            20                  25

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Thr Asn Thr Asn Ser Ser Ser
1               5

<210> SEQ ID NO 8
<211> LENGTH: 19
<212> TYPE: PRT
```

```
<213> ORGANISM: Artificial Sequence
<220> FEATURE:
<223> OTHER INFORMATION: Synthetic Peptide

<400> SEQUENCE: 8

Thr Asn Thr Asn Ser Ser Ser Gly Gln Gln Gln Leu Gly Arg Met Ile
1               5                   10                  15

Met Glu Lys

<210> SEQ ID NO 9
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 9

Trp Phe Asn Ser Thr Trp Gly Gln Gln Gln Leu Gly Ser Thr Glu Gly
1               5                   10                  15

Ser Asn Asn Thr Glu Gly Ser Asp
            20

<210> SEQ ID NO 10
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 10

Trp Phe Asn Ser Thr Trp Gly Asp Ser Leu Asp Met Leu Glu Trp Ser
1               5                   10                  15

Leu Met Ser Thr Glu Gly Ser Asn Asn Thr Glu Gly Ser Asp
            20                  25                  30

<210> SEQ ID NO 11
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 11

Val Lys Leu Thr Pro Leu Cys Val Ser Leu Lys Cys Thr Asp Leu Lys
1               5                   10                  15

Asn Asp Thr Asn Thr Asn Ser Ser Ser Gly Arg Met Ile Met Glu Lys
            20                  25                  30

Gly Glu Ile Lys Asn Cys Ser Phe Asn
        35                  40

<210> SEQ ID NO 12
<211> LENGTH: 46
<212> TYPE: PRT
<213> ORGANISM: Artificial Sequence
<220> FEATURE:
<223> OTHER INFORMATION: Synthetic Peptide

<400> SEQUENCE: 12

Val Lys Leu Thr Pro Leu Cys Val Ser Leu Lys Cys Thr Asp Leu Lys
1               5                   10                  15

Asn Asp Thr Asn Thr Asn Ser Ser Ser Gly Gln Gln Gln Leu Gly Arg
            20                  25                  30

Met Ile Met Glu Lys Gly Glu Ile Lys Asn Cys Ser Phe Asn
```

```
                35                  40                  45

<210> SEQ ID NO 13
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 13

Val Lys Leu Thr Pro Leu Cys Val Thr Leu Asn Cys Lys Asp Val Asn
1               5                   10                  15

Ala Thr Asn Thr Thr Asn Asp Ser Glu Gly Thr Met Glu Arg Gly Glu
            20                  25                  30

Ile Lys Asn Cys Ser Phe Asn
        35

<210> SEQ ID NO 14
<211> LENGTH: 44
<212> TYPE: PRT
<213> ORGANISM: Artificial Sequence
<220> FEATURE:
<223> OTHER INFORMATION: Synthetic Peptide

<400> SEQUENCE: 14

Val Lys Leu Thr Pro Leu Cys Val Thr Leu Asn Cys Thr Asp Val Thr
1               5                   10                  15

Asn Val Thr Asp Val Ser Gly Thr Arg Gly Asn Ile Thr Ile Met Lys
            20                  25                  30

Glu Met Glu Gly Glu Ile Lys Asn Cys Ser Phe Asn
        35                  40

<210> SEQ ID NO 15
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 15

Val Lys Leu Thr Pro Leu Cys Val Thr Leu Gln Cys Thr Asn Val Thr
1               5                   10                  15

Asn Asn Ile Thr Asp Asp Met Arg Gly Glu Leu Lys Asn Cys Ser Phe
            20                  25                  30

Asn

<210> SEQ ID NO 16
<211> LENGTH: 46
<212> TYPE: PRT
<213> ORGANISM: Artificial Sequence
<220> FEATURE:
<223> OTHER INFORMATION: Synthetic Peptide

<400> SEQUENCE: 16

Val Lys Leu Thr Pro Leu Cys Val Ser Leu Lys Cys Thr Asp Leu Lys
1               5                   10                  15

Asn Gly Gln Gln Gln Leu Gly Thr Asn Thr Asn Ser Ser Ser Gly Arg
            20                  25                  30

Met Ile Met Glu Lys Gly Glu Ile Lys Asn Cys Ser Phe Asn
        35                  40                  45

<210> SEQ ID NO 17
```

<211> LENGTH: 52
<212> TYPE: PRT
<213> ORGANISM: Artificial Sequence
<220> FEATURE:
<223> OTHER INFORMATION: Synthetic Peptide

<400> SEQUENCE: 17

Val Lys Leu Thr Pro Leu Cys Val Ser Leu Lys Cys Thr Asp Leu Lys
1               5                   10                  15
Asn Gly Asp Ser Leu Asp Met Leu Glu Trp Ser Leu Met Thr Asn Thr
            20                  25                  30
Asn Ser Ser Ser Gly Arg Met Ile Met Glu Lys Gly Glu Ile Lys Asn
        35                  40                  45
Cys Ser Phe Asn
    50

<210> SEQ ID NO 18
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 18

Thr Trp Ser Thr Glu Gly Ser Asn Asn Thr Glu Gly
1               5                   10

<210> SEQ ID NO 19
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 19

Thr Trp Gly Asp Ser Leu Asp Met Leu Glu Trp Ser Leu Met Ser Thr
1               5                   10                  15
Glu Gly Ser Asn Asn Thr Glu Gly
            20

<210> SEQ ID NO 20
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 20

Thr Trp Asn Asn Asn Thr Glu Gly Ser Asn Asn Thr Glu Gly
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 21

Thr Trp Asn Thr Ser Met Ser Gly Ser Ser Asn Thr Glu Thr
1               5                   10

<210> SEQ ID NO 22
<211> LENGTH: 10
<212> TYPE: PRT

```
<213> ORGANISM: Artificial Sequence
<220> FEATURE:
<223> OTHER INFORMATION: Synthetic Peptide

<400> SEQUENCE: 22

Thr Ser Val Gln Gly Ser Asn Ser Thr Gly
1               5                   10
```

FRET-BASED REAGENTS AND METHODS FOR IDENTIFYING ANTI-HIV COMPOUNDS

CROSS REFERENCE TO RELATED APPLICATIONS

This application claims priority from U.S. Provisional Application No. 61/650,180, filed May 22, 2012, the entire contents of which are incorporated herein by reference.

INCORPORATION BY REFERENCE OF SEQUENCE LISTING

The Sequence Listing in an ASCII text file, named 28816_5942_03_US_SequenceListing.txt of 8 KB, created on Nov. 19, 2014, and submitted to the United States Patent and Trademark Office via EFS-Web, is incorporated herein by reference.

STATEMENT REGARDING FEDERALLY SPONSORED RESEARCH OR DEVELOPMENT

This invention was made with Government Support under Contract No. R21 AI100696 awarded by the NIH/NIAID, and R01 GM079238-06, R01 GM079238-06S1, and R01 GM098859-01 awarded by the NIH. The Government has certain rights in this invention.

FIELD OF THE DISCLOSURE

This invention relates to reagents and methods useful for discovering anti-HIV drugs. In particular, this invention relates to reagents and methods for identifying anti-HIV compounds in a single molecule fluorescence resonance energy transfer (smFRET)-based system.

BACKGROUND ART

HIV-1 Env remains an attractive target for preventive antiviral therapies as it is the only viral protein exposed on the surface of entering HIV-1 virions. Env consists of a trimer of solvent-exposed glycan-covered gp120 domains, each with a transmembrane gp41 stalk. Gp120 contains the receptor and coreceptor binding sites; gp41 comprises the membrane fusion machinery. The conformation of HIV-1 Env is metastable. Binding to CD4 induces conformational changes in gp120, which unmask the coreceptor (CCR5 or CXCR4) binding site. Coreceptor binding activates gp41, which promotes fusion of the viral and cell membranes.

The limited success in targeting HIV-1 Env can be attributed in part to our incomplete understanding of the structural dynamics of the unliganded HIV-1 Env trimer, a lack of understanding of the molecular mechanism of Env activation, and the high sequence variability of Env. Crystallographic studies have concentrated on the monomeric core of gp120 in the absence of gp41, variable loops, and glycans. The HIV-1 gp120 core exists as an ensemble of different conformers in dynamic equilibrium and requires ligands such as receptor CD4, or chemical crosslinking to adopt a single conformation that permits crystallization. It remains unclear to what extent these structures can be extrapolated to the behavior of the Env trimer. While recent electron tomography studies have provided insights into the structure of trimeric Env on the native virus, the resolution remains low (White et al. (2010) PLoS Pathog 6, e1001249; Liu et al (2008) Nature 455, 109-113; Hu et al. (2011) J Virol 85, 2741-2750). Moreover, no dynamic data exist on the sampling of various conformations, their relative stabilities, or the kinetics of the transitions between states. Thus, despite the existence of a wealth of structural information, the HIV-1 Env trimer and the structural dynamics remain poorly understood.

Understanding the conformational trajectories of HIV-1 Env activation by receptor and coreceptor represents a critical prerequisite for the rational design of antiviral therapies that prevent virus fusion. This is particularly important for inhibitors that target the CD4 binding site. While they can function as competitive inhibitors, they may also act as CD4 mimetics to activate HIV-1 Env and promote infection of cells lacking CD4 (Madani et al (2008) Structure 16, 1689-1701; Schön et al (2006) Biochemistry 45, 10973-10980; Haim et al. (2009) PLoS Pathog 5, e1000360). In contrast, allosteric inhibitors can divert Env to conformations that no longer support virus fusion. Consequently, understanding the conformational trajectories underlying activation or inhibition is of critical importance for the development of antiviral therapies.

SUMMARY OF THE DISCLOSURE

This disclosure is directed to establishing a single-molecule FRET imaging system for determining and monitoring conformational states of HIV-1 Env. The smFRET-based methodology disclosed herein enable conformational screening for inhibitory molecules (such as small molecules and antibodies) that block, induce or trap HIV-1 Env in specific conformational states, useful for developing anti-HIV drugs. Accordingly, this disclosure provides a smFRET-based method for screening for conformational HIV inhibitors as well as various compositions and reagents for implementation of such method.

In one aspect, this disclosure provides a modified HIV Env protein containing modifications artificially introduced to gp120 to permit fluorophore labeling.

In one embodiment, the modified En protein includes an artificially introduced first mutation in a first variable loop of gp120, wherein the first mutation includes an insertion of one or more amino acids. In a specific embodiment, the first mutation includes insertion of a first peptide of at least four amino acids in the first variable loop.

In another embodiment, the modified Env protein includes a second mutation in a second variable loop of gp120, wherein the second mutation includes an insertion of one or more amino acids. In a specific embodiment, the second mutation includes insertion of a second peptide of at least four amino acids in the second variable loop.

The first and second variable loops can be independently selected from V1, V2, V3, V4 or V5 of gp120. In one embodiment, the first and second variable loops are V1 and V4, respectively.

The first and second peptides can be the same or different, and can be independently selected from, for example, the S6 tag, the A1 tag, or the Q3 tag. In specific embodiments, the first and second peptides are selected from the A1 tag or the Q3 tag.

In some embodiments, the modified HIV Env protein is a full-length Env protein and includes both gp120 and gp41. In other embodiments, the modified HIV Env protein is composed of gp140, which is a cleaved, soluble version of the ectodomain of HIV-Env.

In another aspect, this disclosure provides nucleic acid molecules encoding modified HIV Env proteins, expression vectors and host cells for making the modified HIV Env proteins and Env trimers including one unit of a modified gp120 protein.

In a further aspect, this disclosure provides isolated Env trimers containing one unit of a modified gp120 (or a modified, soluble gp140) and two units of an unmodified gp120 (or soluble gp140), as well as virions containing such Env trimers. The Env trimers, either in an isolated form or in intact virions, can be labeled with fluorophores at the site of the inserted amino acid(s) or peptides, disclosed herein. The trimers can be labeled at a single site (either at the first or the second mutation), or at a pair of sites (both the first and the second mutations) with a donor fluorophore and an acceptor fluorophore, respectively. The labeled Env trimers or virions can be immobilized on the surface of a solid support for smFRET imaging.

In a further aspect, this disclosure provides a method for identifying the effect of a compound on HIV Env. This method employs the HIV Env trimer disclosed herein, either in isolated form or in an intact virion, subjects the Env trimer to a test compound, and detects the changes in at least one smFRET parameter of the HIV Env trimer, wherein the at least one smFRET parameter is selected from the number of smFRET states, the distribution of smFRET states, and the transitions between smFRET states.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

FIG. 1. Infectivity of HIV-1 viruses containing peptides for labelling within variable loops of gp120. (a) Four different peptides, corresponding to four orthogonal enzymatic labelling strategies, were inserted into various positions within variable loops V1, V2, and V4 of the gp120 domain of HIV-1 Env of full-length HIV-1NL4-3. The peptides considered are denoted S6 (GDSLSWLLRLLN) (SEQ ID NO: 1) (Zhou, Z. et al. ACS Chem Biol 2, 337-346 (2007)), A1 (GDSLDMLEWSLM) (SEQ ID NO: 2) (Zhou, Z. et al. ACS Chem Biol 2, 337-346 (2007)), FGE (LCTPSR) (SEQ ID NO: 4) (Wu, P. et al. Proc Natl Acad Sci USA 106, 3000-3005 (2009)), and Q3 (GQQQLG) (SEQ ID NO: 3) (Lin et al. J Am Chem Soc 128, 4542-4543 (2006)). The infectivity of the singly tagged viruses was measured using a luciferase assay, and is displayed as a percentage of wild-type HIV-1NL4-3. (b) Four insertion sites yielded high enough infectivity so as to warrant further consideration. The amount of tagged pNL4-3 was diluted with varying amounts of wild-type pNL4-3 (1:0, 1:2, 1:9 tagged:wild-type), and the resulting infectivity was measured as before. When moderate effects on infectivity were observed, the infectivity was fully recovered at a ratio of 1:2. This corresponds to ~1 tagged gp120 domain per trimer, indicating that the presence of two wild-type gp120s rescued the infectivity. (c) The peptides inserted into V1 were each combined with the well-tolerated A1 insertion at V4-2, forming three dually tagged viral constructs. These data characterized the V1-1-Q3/V4-2-A1 as the most well behaved dually labelled HIV-1NL4-3. The data are presented as the average of three independent measurements. Error bars represent the standard error. RLU, relative light units.

FIG. 2. Tagged Envs are incorporated into virions, and processed into gp120 and gp41. Viral supernatants from cells generating HIV-$1_{NL4-3}$ containing wild-type and dually tagged Env was collected and centrifuged over a 15% sucrose cushion. The amount of unprocessed gp160, processed gp120, and p24 antigen in the pellet was quantified by Western blot. The molecular weight (in kDa) marker is indicated at left.

FIG. 3. Dually tagged HIV-$1_{NL4-3}$ viruses are neutralized by trimer-specific antibodies. (a,b) Neutralization of the V1-3-Q3/V4-2-A1 virus by the PG16 (a) and PGT145 (b) antibodies. The infectivity of virus with undiluted tagged Env (blue), tagged Env diluted 1:2 with wild-type Env (cyan), and wild-type Env (black), in the presence of increasing concentrations of broadly neutralizing antibodies PG16 and PGT145 (Walker, L. M. et al. *Nature* 477, 466-470 (2011); Walker, L. M. et al. *Science* 326, 285-289 (2009)). The data are displayed as the infectivity relative to control lacking antibody. (c, d) Neutralization of the V1-3-A1/V4-2-A1 virus by the PG16 (c) and PGT145 (d) antibodies. The neutralization sensitivity is fully restored by the presence of two wild-type gp120 domains per trimer, on average. The data are presented as the average of three independent measurements. Error bars represent the standard error. RLU, relative light units.

FIG. 4. Alignments of partial sequences of the variable loops V1 and V4 of gp120 of viral isolates NL4-3 (with and without peptide insertions), JR-FL, KNH1144, and BG505. The numbering is based on HXB2 isolate.

FIG. 5. Surface immobilization of HIV-1 virions. (a) The infectivity of HIV-$1_{NL4-3}$ after incubation with varying concentrations of DSPE($PEG_{2,000}$)-biotin (Mukherjee et al. *Nanotechnology* 20, 065103 (2009)). No loss of infectivity was seen at the concentration used to immobilize virus (0.02 mg/ml). The infectivity is displayed as RLU (relative light units), as a percentage of the no-lipid control. (b) The growth of surface-localized fluorescence due to specific immobilization of fluorescent virions on streptavidin-coated quartz microscope slides observed via TIRF microscopy. Without prior incubation with DSPE($PEG_{2,000}$)-biotin no virus bound the surface.

FIG. 6. Single-molecule FRET imaging reveals that HIV-1 Env is structurally dynamic. (a) Experimental design. Native HIV-1 virions containing a single dually labelled Env molecule among native trimers (blue) were surface immobilized on quartz microscope slides, and imaged with TIRF microscopy. The insert depicts the insertion of organic dyes into the variable loops V1 (green) or V4 (red) of HIV-1 gp120 (PDB IDs 1GC1 and 3DNO) (Kwong et al. *Nature* 393, no. 6686 (1998): 648-59; Liu et al., *Nature* 455, no. 7209 (2008): 109-13). (b) Representative fluorescence (Cy3, green; Alexa647, red) and FRET (blue) trajectories from a single HIV-1 Env molecule. FRET trajectories were compiled into histograms and fit to the sum of three Gaussian distributions with means 0.11±0.01, 0.29±0.01, and 0.71±0.01 (red) (errors indicate 95% confidence intervals). (c, d) Fluorescence and FRET trajectories, and FRET histograms obtained in the presence of sCD4 (D1D2 domains). (c), and in the presence of sCD4 and the 17b Fab (d). (e) The same data obtained from HIV-1 Env containing the mutations D368R and E370R. Each histogram contains 100-150 smFRET trajectories per experiment. Red arrows indicate photobleaching of Alexa647. Error bars represent the standard errors obtained from three independent populations of FRET traces.

FIG. 7. Kinetic analysis of smFRET trajectories. (a) A representative FRET trajectory (blue) overlaid with the idealized trace (red) generated by fitting to a three-state Markov chain (Qin et al. *Biophys J* 86, no. 3 (2004): 1488-501). (b,c) Transition density plots displaying the frequency of observed FRET transitions for the unliganded (b), and sCD4-bound Env (c). (d-g) The distributions of rate constants for transitions between low and high FRET (d,e), and between high and intermediate FRET (f,g), in the absence and presence of sCD4.

FIG. 8. Energy landscape model for the conformational transitions of HIV-1 Env. (a) Three-dimensional landscape indicating the putative order of conformational transitions leading to the activated state. (b) Free-energy profiles for transitions between all observed FRET states in the absence and presence of sCD4. Energies are displayed in units of $k_B T$, where $k_B$ is the Boltzmann's constant, and T is temperature. Error bars represent 95% confidence intervals propagated from the kinetic analysis.

FIG. 9. (a) Experimental setup. (b) Single-molecule fluorescence (Cy3, green; Cy5, red) and FRET (blue) trajectories. (c) Histogram of observed FRET values fit to the sum of three Gaussians. (d) Structural model of the CD4-bound HIV-1 Env trimer (gp120 domains, blue; CD4, pink (2)) with approximate dye positions and inter-dye distances.

Figure 10:
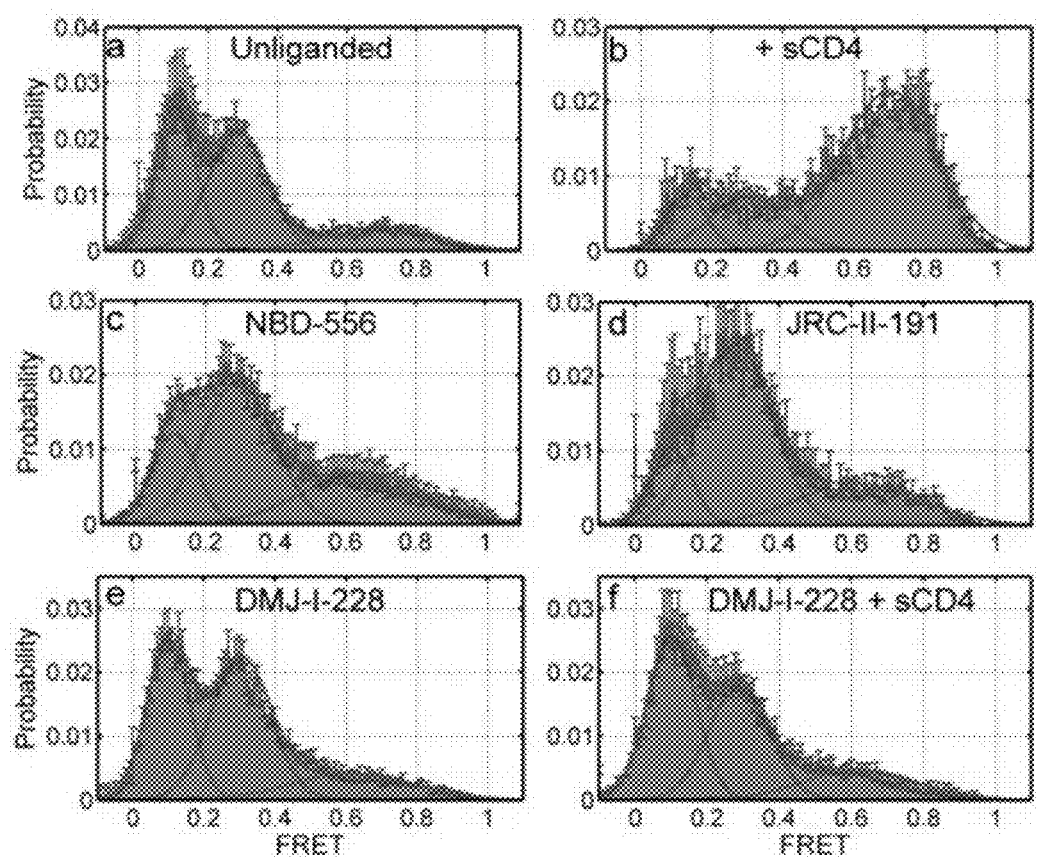

FIG. 10. FRET histograms for the (a) unliganded HIV Env trimer, and with (b) sCD4, (c) NBD-556, (d) JRC-II-191, (e) DMJ-I-228, and (f) DMJ-I-228 and sCD4.

DETAILED DESCRIPTION

The envelope spike protein (Env) of HIV remains an attractive target for preventive antiviral therapies as it is the only viral protein exposed on the surface of entering HIV-1 virions. Success in targeting HIV-1 Env has been thus far limited due to difficulties in determining the molecular mechanism of identified inhibitors, a poor understanding of the structure and the dynamics of the unliganded HIV-1 Env trimer, and a lack of understanding of the molecular mechanism of Env activation and its resulting vulnerabilities.

In this disclosure, the present inventors have successfully demonstrated, by applying single-molecule imaging techniques, the conformation states of HIV-1 Env in its unliganded state and conformational consequences of HIV-1 Env activation by receptor and co-receptor as well as antagonism by small-molecule inhibitors. The introduction of small organic fluorophores at selected positions within HIV-1 Env that do not affect infectivity permits the detection of changes in inter-dye distances as a measure of conformational changes Implementation of the smFRET-based technologies disclosed herein enable conformational screening for inhibitory molecules (such as small-molecule inhibitors or antibodies) that block, induce or trap HIV-1 Env in specific conformational states. Accordingly, this invention provides methods for identifying anti-HIV molecules (such as small-molecule inhibitors or antibodies) in a smFRET-based screening, and various reagents useful for implementation of such methods.

Single-Molecule Fluorescence Resonance Energy Transfer.

"Single-molecule fluorescence resonance energy transfer" (or "smFRET") is the application of FRET techniques to study a single molecule with at least two fluorescent labels, or the interaction of at least two molecules, each with a label. Fluorescence Resonance Energy Transfer (FRET) is a non-radiative pathway by which a molecule in an electronic excited state may relax back to the more stable ground state. The transfer of energy occurs through space via dipole-dipole interaction: energy from the excited-state molecule (the donor fluorophore) may transfer to a neighboring molecule (the acceptor fluorophore) given significant degree of spectral overlap between donor emission and acceptor absorption, properly oriented dipole moments of the interacting dye molecules, and the appropriate distance between the two fluorophores. In smFRET the donor and receptor fluorophores are either on the same molecule, or are on different molecules that interact, bringing the two fluorophores into proximity. The detection of FRET at the single-molecule scale enables the direct measurement of conformational events on biologically-relevant time scales. At least two fluorophores are required.

Dynamic smFRET refers to the use of smFRET techniques to interrogate biological samples of interest over extended periods of time in order to quantify changes in the amount of time that the sample spends in its various conformational states, i.e., the sample's conformational dynamics. An extended period of time for smFRET studies can be a period from 100 milliseconds, or 2-3 seconds, up to at least a minute or over several minutes, depending on the conformational time dynamics of the protein under interrogation.

In accordance with this disclosure, in order to delineate the order and timing of conformational changes of HIV Env, HIV Env are labeled with a fluorophore (a donor or acceptor fluorophore), or with a pair of fluorophores (donor and acceptor), at positions that inform on the conformational changes of Env without affecting function. The donor fluorophore will be under direct excitation by a laser. When the donor is brought within close proximity to the acceptor, energy is transferred from the donor to the acceptor at an efficiency that is dependent on the inter-dye distance. This efficiency is described by the relationship $FRET=1/(1+(R/R_0)^6)$, where R is the inter-dye distance, and $R_0$ is the Förster distance, which determines the scale on which FRET is a sensitive measure of distance. The commonly used cyanine dyes, have an $R_0$ of ~56 Å and a response range of ~30-80 Å, are well suited for the dimensions of the Env trimer. From fluorescence trajectories, the FRET efficiency (or the FRET value) can be calculated according to $FRET=I_A/(I_A+I_D)$, where $I_A$ is the intensity of acceptor fluorescence, and $I_D$ is that of the donor. Observation of FRET provides direct information on the relative movements of the donor and acceptor fluorophores as a function of time. Hundreds to thousands of individual FRET trajectories are recorded simultaneously and analyzed through established computational means (as described, e.g., by Munro et al. (2007) *Mol Cell* 25, 505-517; Munro et al (2010) *Nat Struct Mol Biol* 17, 1470-1477; McKinney et al. (2006) *Biophys J* 91, 1941-1951; Qin et al. (1996) *Biophys J* 70, 264-280), and compiled into FRET histograms to reveal the number and occupancies of the observed FRET states.

Site-Specific Labeling with a Fluorophore

To prepare for smFRET analysis, a protein of interest (e.g., HIV Env gp120/gp41, soluble gp140, or a ligand protein such as CD4) is labeled with a fluorophore (a donor or acceptor fluorophore), or with a pair of fluorophores (donor and acceptor). The labeling can be achieved using various technologies.

A "fluorophore" is a component of a molecule which causes a molecule to be fluorescent. It is a functional group in a molecule which will absorb energy of a specific wavelength and re-emit energy at a specific wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores are derivatives of rhodamine (TRITC), coumarin, pyrene, and cyanine. Newer generations of fluorophores such as maleimide derivative dyes, CF dyes, the FluoProbes dyes, the DyLight Fluors, the Oyester dyes, the Atto dyes, the HiLyte Fluors, and the Alexa Fluors are believed to perform better (more photostable, brighter, and/or less pH-sensitive) than other standard dyes of comparable excitation and emission. A molecule containing a fluorophore is also referred to herein as a "dye".

In specific embodiments, fluorophores from the cyanin family are used in the method disclosed herein. The cyanine dyes, Cy3, Cy5, and Cy7, are well-established for use in smFRET imaging owing to their brightness, photostability, and water solubility (see, e.g., Roy et al. (2008) *Nat Methods* 5, 507-516.). Derivates of cyanine fluorophores with further improved photostability have also been developed and can be used in practicing this invention (Altman et al. (2011) *Nat Methods*; Altman et al. (2012) *Nat Methods* 9, 428-429). Fluorophores combined with one or more fluorophore-protective agents, such as TSQs (triplet state quenchers), in particular Cyclooctatetraene, Trolox and NBA, can be used in practicing the present invention. Such TSQs are described in International Application PCT/US10/24824 (published as US 2010/096720), which is incorporated herein by reference in its entirety.

In specific embodiments, fluorophores from the biarsenical family are used in the method disclosed herein. For example, dyes disclosed in U.S. Pat. No. 7,141,655 entitled "Reagents and procedures for high-specificity labeling", invented by Yon W. Ebright and Richard H. Ebright, and originally assigned to Rutgers, The State University Of New Jersey, and including those FlAsH and ReAsH as published in Griffin B A, Adams S R, Tsien R Y (1998) "Specific covalent labeling of recombinant protein molecules inside live cells", *Science* 281:269-272, or as published in Fu N et al (2012) "Synthesis of a Targeted Biarsenical Cy3-Cy5 Affinity Probe for Superresolution Fluorescence Imaging", *J. Am. Chem. Soc.* 134:18530-18533.

In some embodiments, the protein of interest, either in an isolated form or in the context of intact virions, is labeled with a dye conjugated to a functional group specific to reactive residues such as cysteines or lysines in the protein. A cystein or lysine can be uniquely present in the protein of interest, or can be exogenously introduced to a site in the protein. It may be necessary to remove the remaining cysteins or lysines in the protein to ensure that labeling occurs only at selected and desirable positions.

The introduced amino acid can be a natural amino acid or an unnatural amino acid. A "natural amino acid" refers to an amino acid that is naturally incorporated into polypeptides in organisms. There are 22 natural amino acids, 20 of which are encoded by the universal genetic code. A "non-natural amino acid" refers to an amino acid that is not naturally incorporated into proteins by cellular machinery. Non-natural amino acids include amino acids that are in proteins but are formed by post-translational modification (e.g., hydroxyproline), as well as amino acids that are not found in naturally occurring proteins.

The choice of amino acid being introduced for purposes of labeling may depend on the fluorophore to be attached. For example, if a maleimimide dye is used, a cysteine will be introduced for covalent attachment of the dye. If the protein includes one or more native cysteines, these may be used for labeling. Alternatively, the cysteine residue(s) present in the native membrane protein can be substituted with other suitable amino acids so as not to interfere with the labeling through an introduced cysteine at a selected site. For attachment of other fluorophores, other amino acids mutations can be introduced, including substitution mutations using an unnatural amino acid, using techniques known in the art; see, e.g., Munro, J. B., et al. *EMBO J.* 29(4):770-781 (2010). Fluorophores may also be attached using other chemistries, such as click chemistry (for review of click applications for covalent attachment in biomolecules, see Nwe, K., et al., *Cancer Biother. Radiopharm.* 24(3):289-302 (2009)).

In other, preferred embodiments, a fluorophore can be introduced into a specific site by utilizing an enzymatic labeling method, for example, as described by Zhou et al. (2007) *ACS Chem Biol* 2, 337-346; Lin et al. (2006) *J Am Chem Soc* 128, 4542-4543; and Wu et al. (2009) *Proc Natl Acad Sci USA* 106, 3000-3005.

In specific embodiments, a protein of interest is labeled using one of the following three enzymatic labeling techniques to site-specifically introduce organic dyes. First, bacterial phosphopantetheinyl (PPant) transferases specifically ligate the PPant moiety from coenzyme A (CoA) to 12-amino-acid peptide insertions (Zhou et al. (2007) *ACS Chem Biol* 2, 337-346). The existence of two related enzymes Sfp and AcpS, which specifically recognize the distinct peptides GDSLSWLLRLLN ("S6 tag", SEQ ID NO: 1) and GDSLDMLEWSLM ("A1 tag", SEQ ID NO: 2), respectively, allows the introduction of two different dyes into a single protein. The S3 residue of each peptide is specifically labeled through incubation with purified Sfp or AcpS and a CoA-fluorophore conjugate. Second, guinea pig liver transglutaminase (TGase) recognizes the GQQQLG peptide ("Q3 tag", SEQ ID NO: 3) and catalyzes formation of an amide linkage between a glutamine and a cadaverine-fluorophore conjugate (Lin et al. (2006) *J Am Chem Soc* 128, 4542-4543). Third, formyl glycine generating enzymes (FGE) convert a cysteine embedded within a minimal consensus sequence LCXPXR (SEQ ID NO: 4, with "X" representing any amino acid residue) to formylglycine in the endoplasmic reticulum (Wu et al. (2009) *Proc Natl Acad Sci USA* 106, 3000-3005). The aldehyde group is subsequently site specifically labeled using aminooxy- or hydrazide-fluorophore conjugates. The enzymes involved are either readily available, or can be made recombinantly and purified for use in labeling reactions; for example, bacterial phosphopantetheinyl (PPant) transferases Sfp and AcpS can be made using expression plasmids described in Zhou et al. (2007) *ACS Chem Biol* 2, 337-346, guinea pig liver TGase can be purchased from Sigma, and FGE can be made using a plasmid described in Rabuka et al., *Nat Prot* 7, 1052-1067 (2012).

Positioning of Fluorophore Labels within a Protein of Interest

Generally speaking, the fluorophore labels should be introduced to a protein under examination at positions that inform on the conformational changes of the protein without affecting function.

For example, for HIV Env, to ensure that a modified Env containing a labeling peptide still assumes the conformation and function of a native/unmodified Env, the following criteria are considered and can be assessed. First, infectivity of labelled viruses, which can be determined in a luciferase-based infectivity assay for example, remain within at least 80%, 85% or 90% of wild-type levels. Second, Env of tagged viruses are processed normally into gp120 and gp41 and incorporated into virions. Third, labelled Env molecules are recognized by the trimer-specific antibodies PG16 and PGT145, which reflects that tagged viruses maintain their native quaternary structure. Finally, sufficient fluorescent labelling efficiency of the modified Env is achieved.

In accordance with this disclosure, the labeling peptides can be inserted into "variable loops" of gp120. Gp120 has five variable loops, V1-V5; and according to the annotated HXB2 sequence in the Los Alamos Database, V1 is composed of amino acids 101-126, V2 is composed of amino acids 127-165, V3 is composed of 266-300, V4 is composed of 355-387, and V5 is composed of 430-439, all in HXB2 numbering. According to this disclosure, the variable loops are regions that can tolerate peptide insertions without affecting the function of gp120. In certain embodiments, labeling peptides are placed in V1, V2, V3, V4 and/or V5. In specific embodiments, labeling peptides are placed in V1 and/or V4.

In addition to considerations for maintaining the conformation and function of a native protein, the labels and the labeling peptides are placed at positions to inform on the conformational changes of the protein. For example, for analyzing the conformational changes of Env trimer, two dyes are placed at positions within gp120 so that changes in the relative distance between the two dyes can report on critical conformational changes induced by receptor and coreceptor binding. In accordance with this disclosure, one fluorescent label can be placed within a more dynamic loop such as V1, V2 or V3, and the second label can be placed in the relatively stationery loop V4. Such placement can effectively report the conformational changes of Env trimer induced by receptor and coreceptor binding which are expected to extend over a distance ideally suited for smFRET (20-50 Å).

In some embodiments, a label is introduced into the V1 loop of gp120 of an HIV Env protein, for example, through a labeling peptide placed within the V1 loop of gp120.

In a specific embodiment, HIV-1 Env may be labeled in the V1 loop of gp120 at a position after the amino acids "DLKN" (with "N" being amino acid position 106 based on HXB2 numbering for HIV strain NL4-3 following the removal of the N-terminal signal sequence) and before amino acids "TN" (with "T" being amino acid position 108), or a corresponding position in another HIV isolate.

By "HXB2 numbering" it is meant the amino acids remaining after the removal of the signal sequence are numbered based on the first HIV molecular clone, HXB2, which is nearly identical with NL4-3.

By "corresponding position" in another HIV isolate, it means an amino acid position of the Env protein in such other isolate that aligns between position 106 and 108 of the Env protein of HIV strain NL4-3 when the protein sequences of the Env proteins of the viral isolates are paired up, either based on eye comparison or by a computer program. FIG. 4 shows sequence alignments of portions of V1 and V4 of the gp120 proteins of NL4-3, with and without peptide insertions, along with sequences from three other isolates, JR-FL, KNH1144 and BG505.

For example, a labeling amino acid residue (e.g., cystein or lysine) or a labeling peptide (such as the Q3 or the A1 labeling peptide) can be inserted at this position. Modified HIV-1 Env resulting from an insertion of Q3 or A1 contains the sequence: CTDLKN-GQQQLG-TNTNSSSG (SEQ ID NO: 5), and CTDLKN-GDSLDMLEWSLM-TNTNSSSG (SEQ ID NO: 6), respectively.

In another specific embodiment, HIV-1 Env may be labeled in the V1 loop of gp120 at a position immediate after (i.e., within one or two amino acids of) the amino acids "TNTNSSS" (SEQ ID NO: 7) ("S" representing amino acid position 114 based on HXB2 numbering and following removal for the N-terminal signal sequence), or a corresponding position in another HIV isolate. For example, a labeling amino acid residue (e.g., cystein or lysine) or a labeling peptide (such as the Q3 or the A1 labeling peptide) can be inserted at this position. For example, the Q3 peptide can be inserted at this position, and the resulting sequence of the modified HIV-1 Env carrying this insertion in V1 is: TNTNSSS-GQQQLG-RMIMEK (SEQ ID NO: 8).

In other embodiments, a label is introduced into the V4 loop of an HIV Env protein, for example, through a labeling amino acid residue or peptide placed within the V4 loop of gp120.

In a specific embodiment, HIV-1 Env may be labeled in the V4 loop at a position immediately after the amino acid position 400 based on HXB2 numbering, or a corresponding position in another HIV isolate. The resulting sequence of the modified HIV Env contains WFNSTW-GQQQLG-STEGSNNTEGSD (SEQ ID NO: 9 for insertion of Q3; or, WFNSTW-GDSLDMLEWSLM-STEGSNNTEGSD (SEQ ID NO: 10) for insertion of A1.

In specific embodiments, a first labeling amino acid or peptide is placed in the V1 loop of gp120, and a second labeling amino acid or peptide is placed in the V4 loop of gp120. The first and second labeling peptides can be independently selected and can be the same or different peptides, for example, A1/A1, A1/Q3, Q3/A1, Q3/Q3 for V1/V4.

Nucleic Acids, Expression Vectors and Host Cells for Producing Modified Env Proteins or Virions Containing Modified Env Proteins Modified Env proteins or virions containing modified Env proteins can be made using recombinant expression techniques.

By "modified Env protein" it is meant an Env protein containing one or more artificially introduced mutations (e.g., addition of one or more amino acids or peptides for fluorophore labeling, and deletion of one or more amino acids where needed to accommodate the insertion of one or more labeling amino acids or peptides). By "one or more" amino acids, it is meant two, three, four, five, six, or more amino acids, which can be contiguous or separate. The Env protein can be a full length Env (gp120/gp41 processed from the gp160 precursor), or a soluble version composed of the ectodomain of a full length Env (also referred to herein as gp140). As described above, the mutation(s) can be introduced into the gp120 part of either the full length or soluble version of the Env protein.

To this end, genome sequences for a large number of HIV isolates are made publicly available by the Los Alamos National Laboratory, as well as by the National Institutes of Health (NIH) via its NCBI web site. The NIH also makes available to researchers plasmid DNA encoding the Env gene from numerous isolates, as well as plasmid DNA encoding a number of complete genomes, via the AIDS Reagents Program.

A nucleic acid sequence encoding a modified Env protein can be subcloned into an expression vector capable of making the modified Env protein along, or making whole HIV virions containing modified Env proteins, in a host cell. Both isolated or substantially purified trimeric Env proteins and HIV virons containing modified Env trimers can be used in smFRET analysis.

Vectors suitable for recombinant production of modified Env protein or HIV virions are widely available in the art, and include for example, pcDNA3, pCI, pCAGGS, and pCMV. The vectors encoding a modified Env protein and a full length HIV variant can be introduced into appropriate host cells via standard transfection. Examples of host cells suitable for use herein include HEK293 or HEK293T. To obtain Env trimers containing only one modified Env molecule suitable for smFRET analysis, a host cell is transfected with both an expression vector encoding a wild type Env (or a wild type full length viral genome) and an expression vector encoding a modified Env (or a modified full length viral genome) with the wild type vector in excess relative to the modified vector, at a ratio of at least 2:1, 5:1, 10:1, 20:1, or 40:1. The recombinantly expressed Env proteins or virions can be harvested and purified from the supernatants, and are subjected to fluorophore labeling.

Immobilizing Virions for TIRFM

HIV-1 virions are immobilized on a solid support for TIRF imaging.

In some embodiments, to immobilize and spatially separate individual HIV-1 virions for TIRF imaging, biotin-lipid conjugates containing a polyethyleneglycol spacer can be introduced into the viral membrane to facilitate surface tethering via a biotin-streptavidin interaction, as further disclosed in the examples.

In other embodiments, soluble and tagged gp140 trimer constructs that can be immobilized directly using tags. The use of soluble HIV-1 Env trimers facilitates the implementation of high-throughput capabilities. Soluble (SOSIP) gp140 trimers for the HIV-1 strains JR-FL and KNH1144 have been generated and validated (Harris et al., *Proc Natl Acad Sci USA* 108, 11440-11445 (2011); Beddows et al., Virology 360, 329-340 (2007); Beddows et al., *AIDS Res Hum Retroviruses* 22, 569-579 (2006); Sanders et al., *J Virol* 76, 8875-8889 (2002)). The trimer is stabilized by introduction of a disulfide-bond between gp120 and gp41 and by the I559P substitution within the N-terminal heptad repeat in gp41. Proteolytic processing can be enhanced by introduction of a Hex-Arg (R6) motif. Antibody neutralization and structural analysis have revealed that these reagents faithfully mimic the CD4-induced conformational changes within gp120 (Harris et al., *Proc Natl Acad Sci USA* 108, 11440-11445 (2011); Beddows et al., Virology 360, 329-340 (2007); Beddows et al., *AIDS Res Hum Retroviruses* 22, 569-579 (2006); Sanders et al., *J Virol* 76, 8875-8889 (2002)). smFRET probes are introduced into constructs expressing soluble trimers at the positions corresponding to those of the native gp160 Env. To facilitate the immobilization of dually labelled soluble gp140 trimers C-terminal His or Strept tags can be introduced. Passivated microscope slides can be coated with streptavidin, followed by activation with Ni-charged biotin-NTA. The Env trimers can be surface-immobilized via coordination of the Ni cation by the His tag, proven to be a valuable strategy in several systems (Roy et al., *Nat Methods* 5, 507-516 (2008))

Three-Color smFRET

In additional embodiments, three-color smFRET is utilized to provide information on multiple conformational or compositional changes simultaneously. In these embodiments, HIV-1 Env is dually labeled as described above, and a ligand which binds HIV Env (such as CD4 or 17b) is labeled with an additional fluorophore. Thus, a three color smFRET can be set up to have, for example, Cy3, Cy5, and Cy7 (e.g., with Env labeled with Cy3 and Cy5, and a ligand labeled with Cy7); Cy2, Cy3, and Cy5; Cy3, Cy5 and Cy5.5. Three-color smFRET allows monitoring of the conformational dynamics in gp120 in parallel with direct observation of ligand or inhibitor binding.

Drug Discovery

In a further aspect, the smFRET methodology disclosed herein is applied to characterize test compounds for identifying and discovering anti-HIV compounds.

A "test compound", as used herein, may be a small molecule, a nucleic acid, such as RNA or DNA, with or without modified base units or backbones, a peptide or protein, with or without unnatural amino acids and which may be an antibody; a peptide mimetic, a cell, or any other chemical or entity that may be administered to treat or prevent disease.

In some embodiments, a test compound is a small molecule compound. Small molecules include organic compounds, organometallic compounds, salts of organic and organometallic compounds, saccharides, amino acids, and nucleotides. Small molecules typically have molecular weights less than approximately 1500, 1200 or 1000 Daltons, and in some embodiments less than 800 Daltons. Small molecules include compounds that are found in nature as well as synthetic compounds.

By "characterizing" a test compound in a smFRET assay, it is meant to assess the impact of the test compound on a smFRET parameter exhibited by a protein of interest, e.g., HIV Env.

"smFRET parameters" refer to characteristics of a biomolecule shown or determined from a smFRET analysis and include, for example, the number of smFRET states, frequencies/distributions of the smFRET states, transitions from one smFRET state to another and the rates of the transitions.

The term "smFRET state" reflects a conformation or a group of conformations of the underlying biomolecule having an observed FRET value. The number of smFRET states refers to the number of different smFRET states observed for a biomolecule in question. For example, as shown in FIG. 6(b), the unliganded HIV Env trimer is identified as spontaneously transitioning between three distinct FRET states: low (0.11±0.01), intermediate (0.29±0.01), and high FRET (0.71±0.01), corresponding to three distinct conformations characterized by inter-fluorophore distances of ~70 Å, 55 Å and 45 Å, respectively.

The "distribution" of FRET states reflects the proportion of time a molecule spends in each smFRET state. Alternatively, the distribution reflects the probability of finding a molecule in a particular smFRET state. For example, one can compare FIG. 6c with FIG. 6b, and conclude that the distribution of FRET states has been changed upon binding by the ligand, i.e., soluble CD4 (sCD4). More HIV Env trimers are in the high FRET state in the presence of soluble CD4 as compared to in the absence of the ligand. In other words, the binding of soluble CD4 promotes and stabilizes the conformation of Env characterized by the high FRET (also referred to as the CD4-stabilized state). Similarly, by comparing FIG. 6d with FIG. 6b, one can conclude that CD4/17b has changed the distribution of FRET states and stabilizes the intermediate FRET state, also referred to as the "coreceptor-stabilized state".

A transition from one FRET state to another is also observed in smFRET analysis and reflects a conformational change of the molecule from one conformation to another. The transition rate can be taken as the frequency at which a particular transition from one state to another is observed. Transitions from high to intermediate and low FRET states, as well as from intermediate to high FRET state are observed in FIG. 6b; the same transitions are observed in FIG. 6c, although at different frequencies. The evident transitions between these states indicate that the unliganded trimeric HIV-1 Env on the surface of intact virions is intrinsically dynamic, and spontaneously samples minimally three conformations. It is also shown herein, however, that the HIV Env machinery is unable to directly transition from the low FRET state (the ground state) to a coreceptor stabilized intermediate FRET state. Rather, HIV Env requires transition through a CD4-stabilized high FRET state to reach that intermediate FRET state.

smFRET parameters of a given protein can be established prior to testing a compound. For example, in order to delineate the smFRET parameters of HIV Env, HIV Env trimers in a purified form or in the context of whole virions are labeled with a pair of fluorophores (donor and acceptor). The Env trimers or virions are immobilized on a solid support (e.g., slides suitable for use in imaging), and imaged using, for example, total internal reflection fluorescence (TIRF) microscopy. TIRF microscopy affords a high signal to noise ratio, and allows for the observation of conformational transitions over extended periods of time. Essentially, the donor fluorophore is excited by a laser, and energy is transferred to the acceptor according to the relationship $FRET=1/(1+(R/R_0)^6)$, where R is the inter-dye distance, and $R_0$ is the Förster distance. Fluorescence emissions from both the donor and the acceptor are recorded. The FRET efficiency (or the FRET value) can be calculated according to $FRET=I_A/(I_A+I_D)$, where $I_A$ is the intensity of acceptor fluorescence, and $I_D$ is that of the donor. Observation of FRET provides direct information on the relative movements of the donor and acceptor fluorophores as a function of time. Hundreds to thousands of individual FRET trajectories are recorded simultaneously and analyzed through established computational means (as described, e.g., by Munro et al. (2007) *Mol Cell* 25, 505-517; Munro et al (2010) *Nat Struct Mol Biol* 17, 1470-1477; McKinney et al. (2006) *Biophys J* 91, 1941-1951; Qin et al. (1996) *Biophys J* 70, 264-280), and compiled into FRET histograms to reveal the number and occupancies of the observed FRET states. Once population FRET histograms have been compiled to reveal the number and occupancies of the observed FRET states, Hidden Markov modeling can then be used to determine the rates of interconversion between distinct FRET states. The relative occupancies of distinct FRET states reports on the energetic differences between states. The smFRET parameters for a given protein (e.g., gp120 or gp41) can be established in the absence or presence of a ligand (e.g., CD4 or 17b for gp120), which facilitates matching of the smFRET states with functional conformations, as illustrated in the Examples section below.

To characterize the impact of a test compound on a given protein, e.g., Env, smFRET analysis is conducted in the present of the test compound and compared to an analysis conducted in the absence of the compound. Possible impacts include change in the distribution to favor a particular FRET state (including stabilizing or destabilizing a particular state), and/or change in the rate of transition among the states, and induction of a new FRET state, for example. When a compound changes the FRET distribution, the rates of transition among the states will typically also be changed. The reverse is not necessarily true. Generally speaking, insofar as the observed conformational changes are relevant in the function of Env, potentially any change in the Env conformational equilibrium could be deleterious to viral entry into cells.

As illustrated in the Examples herein below, a variety of inhibitors have been assessed in the smFRET analysis disclosed herein, including CD4 mimetics which are generally designed to bind to gp120 in place of CD4 and inhibit entry of HIV into cells. Among these CD4 mimetics, NBD-556 and JRC-II-191 both are shown herein to change the FRET distribution of HIV Env, favoring an intermediate-FRET state. See FIG. 10. Characterization of known inhibitors provides signature smFRET parameters, which can be used as basis for characterization and improved design of new compounds.

The smFRET methodology disclosed herein allows determination of and distinctions between the conformational consequences within gp120 that are induced by CD4 mimetics, allosteric activators, and competitive or allosteric blockers. For example, allosteric activators are expected to mimic the effect of CD4 on HIV-1 Env conformation (e.g., by changing the distribution to favor the high FRET state). In contrast, allosteric blockers or diverters are expected to arrest HIV-1 Env in the preactivated ground-state conformation; function as pure competitive inhibitors with little conformational effects; or divert HIV-1 Env into conformations that are off-pathway for viral entry, and from which the activated state cannot be reached.

The smFRET methodology disclosed herein also allows identification of HIV-1 Env inhibitors that block the formation of the CD4 or co-receptor activated conformational states. Towards this end, the conformational state of HIV-1 Env can be monitored in the absence and presence of soluble CD4 and small molecule inhibitors be identified that inhibit this transition.

In some specific embodiments, the smFRET analysis disclosed herein is applied to identify compounds that stabilize the low-FRET state (also referred to as the ground state conformation). Antibodies isolated from HIV-infected people that target Env and inhibit entry into cells have been shown to have this effect.

In other embodiments, the smFRET analysis disclosed herein is applied to identify compounds that induce inactivated conformations, from which viral entry cannot be achieved. For example, this may manifest as the promotion of an intermediate FRET state as seen for some of the CD4 mimetic compounds (e.g. NBD-556 and JRC-II-191), and which may differ from that state promoted by CD4/17b.

The present description is further illustrated by the following examples, which should not be construed as limiting in any way. The contents of all cited references (including literature references, issued patents, and published patent applications as cited throughout this application) are hereby expressly incorporated by reference.

Example 1. Materials and Methods

Methods Summary

All HIV-1 virions were generated by transfection of pNL4-3-based plasmids in HEK293T cells. Virus was harvested 24 h post-transfection and concentrated by centrifugation. Dually tagged viruses were site-specifically labelled at each peptide insert simultaneously through incubation with appropriate fluorophore conjugates and labelling enzymes. The viruses were purified away from unbound dye by density-gradient ultracentrifugation. Viruses were immobilized on streptavidin-coated quartz microscope slides, and imaged with a lab-built prism-based TIRF microscope equipped with multiple laser. Donor and acceptor fluorescence were separated with a dichroic filter, and imaged on parallel EMCCD cameras. All analysis was carried out with custom-designed Matlab software.

Construction and Testing of Tagged Viruses

All peptides were inserted directly into the gp120 domain of HIV-1$_{NL4-3}$ using overlap-extension PCR. The infectivity of the modified viruses was determined using a luciferase assay (Mazurov et al., *PLoS Pathog* 6, no. 2 (2010): e1000788). Briefly, HEK293T cells were transfected with tagged and/or wild-type pNL4-3 and a Gaussia luciferase reporter construct (HIV-1-inGLuc) at a ratio of 6:1. Virus was harvested 24 h post-transfection, concentrated 10-fold by centrifugation over a 15% sucrose cushion, and titered on MT4 cells. 36 h post-infection, the luciferase activity in the cell supernatant was measured using the BioLux Gaussia Luciferase Assay Kit (New England Biolabs).

Purification and Labelling of Tagged Viruses

The tagged Envs (V1-3-Q3/V4-2-A1 and V1-3-A1/V4-2-A1) were subcloned from pNL4-3 into a pNL4-3 construct lacking reverse transcriptase (pNL4-3 ΔRT). Virus for smFRET experiments was generated by co-transfecting HEK293T cells with tagged-Env-containing pNL4-3 ΔRT and a 40-fold excess of wild-type-Env containing pNL4-3 ΔRT. Virus was harvested 24 h post-transfection and concentrated by centrifugation over a 15% sucrose cushion.

All virus labelling reactions were carried out in buffer containing 50 mM HEPES pH7.5, 10 mM MgCl$_2$, 10 mM CaCl$_2$. Virus containing the V1-3-Q3 and V4-2-A1 peptide insertions was labelled by incubation with 0.5 μM AlexaFluor647-cadaverine (Invitrogen), 0.5 μM Cy3-coenzyme A (Cy3-CoA), 0.65 μM transglutaminase (Sigma) (Lin et al., *J Am Chem Soc* 128, no. 14 (2006): 4542-3), and 5 μM AcpS (Zhou et al., *ACS Chem Biol* 2, no. 5 (2007): 337-46) for 2 h at 37° C. Alternatively, virus containing the V1-3-A1 and V4-2-A1 peptide insertions was labelled by incubation with 0.5 μM Cy5-CoA, 0.5 μM Cy3-CoA, and 5 μM AcpS for 2 h at 37° C. In either case, DSPE-PEG$_{2,000}$-biotin (Avanti Polar Lipids) was then added to a final concentration of 6 μM, and the mixture was incubated for an additional 30 minutes at room temperature. The labelled virus was then purified away from unbound dye and lipid by ultracentrifugation for 1.5 h at 150,000×g over a 6-18% Optiprep (Sigma) gradient in 50 mM Tris pH 7.4, 100 mM NaCl.

smFRET Imaging

Fluorescently labelled virus, containing DSPE-PEG$_{2,000}$-biotin in the viral membrane was immobilized on passivated streptavidin-coated quartz microscope slides and imaged on a lab-built prism-based TIRF microscope. The donor fluorophore was excited with a 532 nm laser (Laser Quantum). Donor and acceptor fluorescence were collected through a high-NA objective, separated with a 650DCXR dichroic filter (Chroma), and imaged on two parallel EMCCD cameras (Photometrics). Movies of surface-immobilized viruses were recorded at 25 frames/s for 40 s at room temperature. All smFRET imaging experiments were performed in buffer containing 50 mM Tris pH7.5, 100 mM KCl, and a cocktail of triplet-state quenchers (Dave et al., *Biophys J* 96, no. 6 (2009): 2371-81). Also included in the imaging buffer were 2 mM protocatechuic acid, and 8 nM protocatechuate 3,4-dehydrogenase for removal of molecular oxygen.

Analysis of smFRET Data

All processing and analysis of fluorescence and smFRET trajectories was carried out using custom-designed Matlab (Mathworks) software. Fluorescence trajectories were extracted from the recorded movies and used to calculate FRET efficiency according to FRET=$I_{Cy5}/(I_{Cy3}+I_{Cy5})$, where $I_{Cy5}$ and $I_{Cy3}$ are the intensities of Cy5 and Cy3 fluorescence, respectively. All trajectories that displayed transitions in FRET were compiled into histograms, and fit to the sum of three Gaussian distributions. The mean of each Gaussian was used to estimate the distance between the approximate locations of the fluorophores according to the relationship FRET=$1/(1+(R/R_0)^6)$. All kinetic and thermodynamics analyses was performed on trajectories obtained from the V1-3-A1/V4-2-A1-labelled Env because they displayed longer-lived fluorescence, which yielded greater numbers of FRET transitions than the traces obtained from V1-3-Q3/V4-2-A1-labelled Env. smFRET trajectories were fit to a 3-state Markov chain model using a segmental k-means algorithm (Qin, *Biophys J* 86, no. 3 (2004): 1488-501). The dwells identified in each FRET state were used to construct TDPs (McKinney et al., *Biophys J* 91, no. 5 (2006): 1941-51), and compiled into histograms. To estimate the rates of interconversion between FRET states, survival probability distributions were fit to the exponential function p(t)=∫a(k) exp(-kt)dk, where a(k) is the distribution in rate constants shown in FIG. 7d-g, using the maximum entropy method (Skilling et al., *Mon Not R Astr Soc* 211 (1984): 111-24). 95% confidence intervals were derived from the residuals of the fits. Free energies were calculated from the occupancies in the observed FRET states estimated through Gaussian fitting of the FRET histograms according to $\Delta G_i = -k_B T \ln P_i$, where $P_i$ is the equilibrium probability of finding the system in the ith FRET state. Changes in activation energies upon addition of sCD4 for transition from state i to state j were estimated according to, for example, $\Delta \Delta G_{ij} = -k_B T \ln (k_{ij}^{sCD4}/k_{ij}^{unliganded})$ where $k_{ij}$ is the weighted average of the distribution of rate constants determined from maximum entropy fitting of the survival probability distributions. The 95% confidence intervals from the survival probability fitting were propagated through these calculations to estimate the uncertainties in energy determination.

Structural Analysis

X-ray crystal structure fittings of EM data as well as EM map adjustments were performed with the Chimera software package. The VRC01 or VRC03 bound EM maps (EMD5457, EMD5458) were fit with X-ray crystallographic structures 3NGB and 3SE8, respectively. The sCD4-bound HIV-1$_{BAL}$ Env map EMD5455 was fit by five different crystal structures (1RZJ, 1RZK, 2QAD, 3LQA and 2B4C) comprised of gp120, sCD4 and a Fab. Antibody coordinates were removed prior to fitting the structures to the density maps. EM density of the HIV-1$_{BAL}$ spike bound by sCD4 and 17b (EMD5023) was fit by the two available atomic level structures with both ligands (1RZJ and 1RZK). A map of the unliganded HIV-1$_{BAL}$ spike EMD5022 was used for the representation of the ground state figures after alignment with VRC01 and VRC03-bound maps that were adjusted by removal of the Fab density. Map densities of liganded structures were adjusted by generating density from atomic level structures of the fitted ligands at equivalent resolutions and subtracting from the EM density. The size of a sphere approximating V1/V2 was determined from the volume occupied by a protein of V1/V2 mass of and density 1.7 g/cm$^3$.

Example 2. Establishing smFRET for the X4-Tropic HIV-1 Env$_{NL4-3}$

To establish smFRET for monitoring the conformational dynamics for the X4-tropic HIV-1 Env$_{NL4-3}$, several viral and technological challenges were considered and addressed. First, in order to yield new information on HIV-1 Env in the context of the native trimer, full-length pNL4-3 clones were used. The incorporation of a single Env molecule labeled with two dyes into otherwise unlabeled HIV-1 virions was possible by transfecting pNL4-3 plasmid encoding for HIV-1 Env$_{NL4-3}$ carrying peptide insertions in the presence of excess (>40-100×) wild-type HIV-1 pNL4-3 plasmid. This ensured that each HIV-1 particle carried maximally one dually labeled Env molecule. Second, the two dyes were placed at positions within gp120 so that changes in the relative distance between the two dyes can report on critical conformational changes induced by receptor and coreceptor binding. Recent electron tomography studies suggested that the trimer is stabilized by the V1/V2 loops at the tip, distal to the viral membrane and gp41 at the base ((White et al. (2010) *PLoS Pathog* 6, e1001249; Liu et al. (2008) *J Virol* 85, 2741-2750). Structural models suggest that upon interaction with CD4, LV1/2 loops undergo a dramatic movement of at least 15 Å (White et al. (2010) *PLoS Pathog* 6, e1001249; Liu et al. (2008) *Nature* 455, 109-113). Likewise, LV3 moves towards the coreceptor. Addition of antibody 17b, which binds the coreceptor-binding site, induces further conformational changes (Liu et al. (2008) *Nature* 455, 109-113). We therefore concluded that one fluorescent probe could be placed within either the dynamic LV1/2 or LV3 loops relative to a reference point such as LV4. The expected conformational changes would extend over a distance ideally suited for smFRET (20-50 Å). Third, while previous work has demonstrated the tolerance of antibody epitopes within variable exposed loops LV1-4 of gp120 (Xiang et al. (2010) *J Virol* 84, 3147-3161; Ren et al. (2005) *J Virol* 79, 5616-5624; Laird et al. (2007) *J Virol* 81, 10838-10848; Leung et al. (2008) *Cell Host Microbe* 3, 285-292), peptide insertions for these novel enzymatic labeling were never tested before and would need to remain accessible to the labeling enzymes. Finally, for visualization by TIRFM, virions harboring single dye molecules need to be immobilized on the surface of quartz microscope slides.

Functional HIV-1 Spikes with a Site-Specifically Labelled Gp120 Domain

Figure 2:
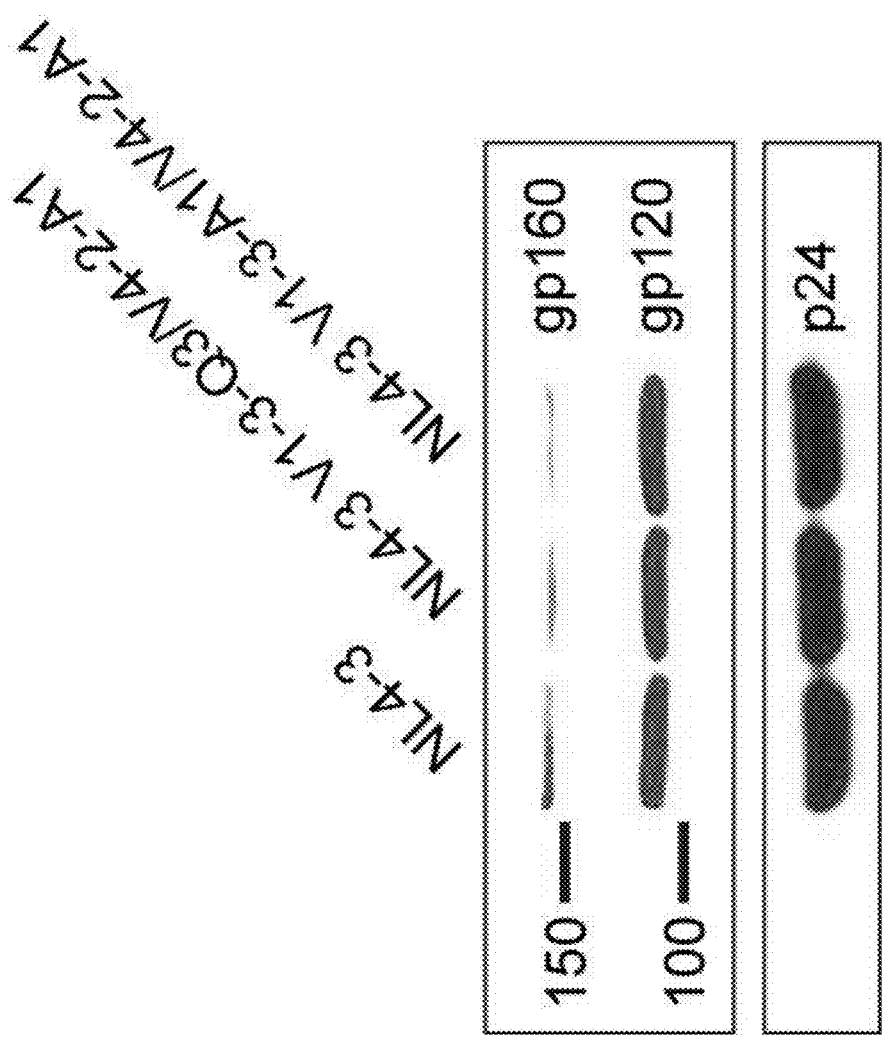
Figures 3A, 3B, 3C, 3D:
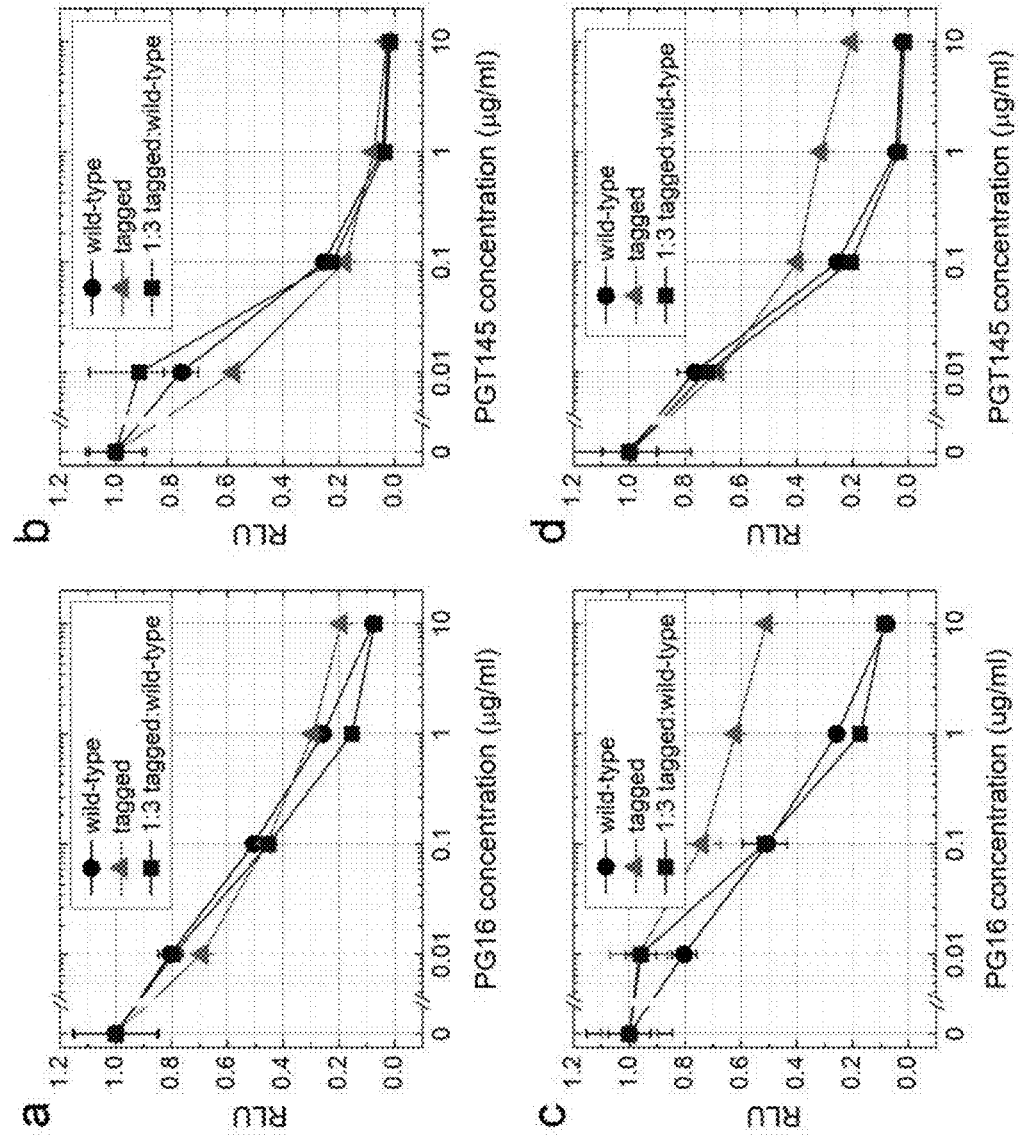

We introduced one fluorophore into the V1/V2 loop; the second fluorophore, which serves as a reference point, was introduced into the V4 loop on the gp120 outer domain, proximal to the initial site of CD4 attachment. Peptides (6-12 amino acids) that allow site-specific enzymatic labelling (Lin et al., *J Am Chem Soc* 128, no. 14 (2006): 4542-3; Zhou et al., *ACS Chem Biol* 2, no. 5 (2007): 337-46) were inserted into various positions within the V1/V2 and V4 loops of gp120 of HIV-1 Env. To enable smFRET studies on the intact HIV-1 virus, these insertions were introduced into the context of full-length HIV-$1_{NL4-3}$. The tagged viruses were evaluated based on four criteria. First, infectivity of the singly and dually labelled viruses as determined with a luciferase-based infectivity assay needed to remain within 90% of wild-type levels (FIG. 1). Second, Env of tagged viruses were required to be processed normally into gp120 and gp41 and incorporated into virions (FIG. 2). Third, recognition of labelled Env by the trimer-specific antibodies PG16 and PGT145 was required to ensure that tagged viruses maintained their native quaternary structure (FIG. 3) (Walker et al., *Nature* 477 (2011): 466-70; Walker et al., *Science* 326, no. 5950 (2009): 285-9). Finally, sufficient fluorescent labelling efficiency of the modified Env needed to be achieved. Two dually tagged viruses which met these criteria were selected (FIG. 4). One virus contained the Q3 peptide (GQQQLG) (SEQ ID NO: 3) in the V1 loop, and the A1 peptide (GDSLDMLEWSLM) (SEQ ID NO: 2) in the V4 loop. The second virus contained A1 in both the V1 and V4 loops.

Figures 5A, 5B:
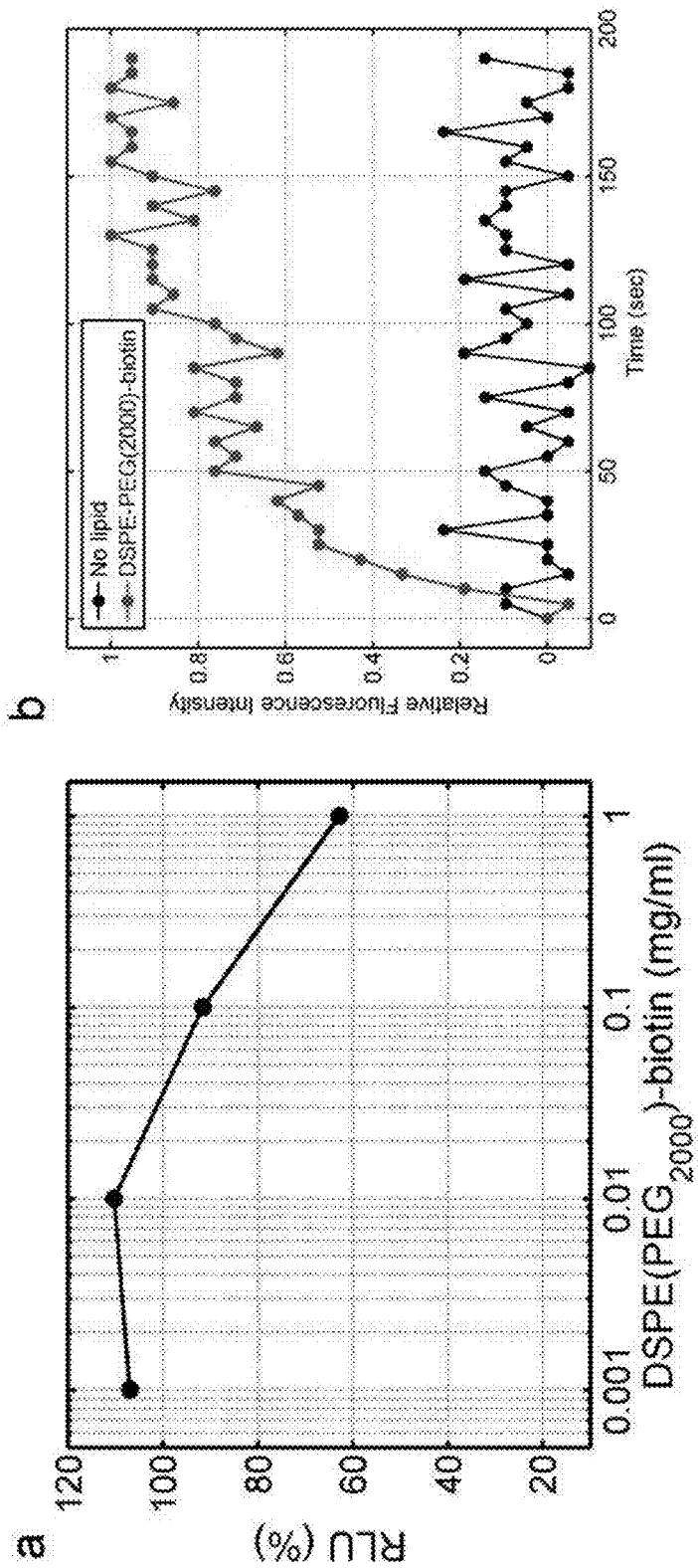

To ensure that only a single fluorescently labelled gp120 molecule was present on the surface of the virus, wild-type pNL4-3 was cotransfected at a ratio of 40:1 over the dually-tagged pNL4-3 during generation of the virus. These viruses were harvested, enzymatically labelled, and purified away from unbound dye as described in Methods. A biotin-lipid conjugate was incorporated into the viral membrane to facilitate immobilization on passivated streptavidin-coated quartz microscope slides (Mukherjee et al., *Nanotechnology* 20, no. 6 (2009): 065103). The incorporation of the lipid had negligible effect on the infectivity of the virus (FIG. 5). The immobilization of the virus was specific, as negligible surface-localized fluorescence was observed in the absence of the biotin-lipid conjugate.

HIV-1 Spike Transitions Between Three Distinct Conformations

Figure 6A:
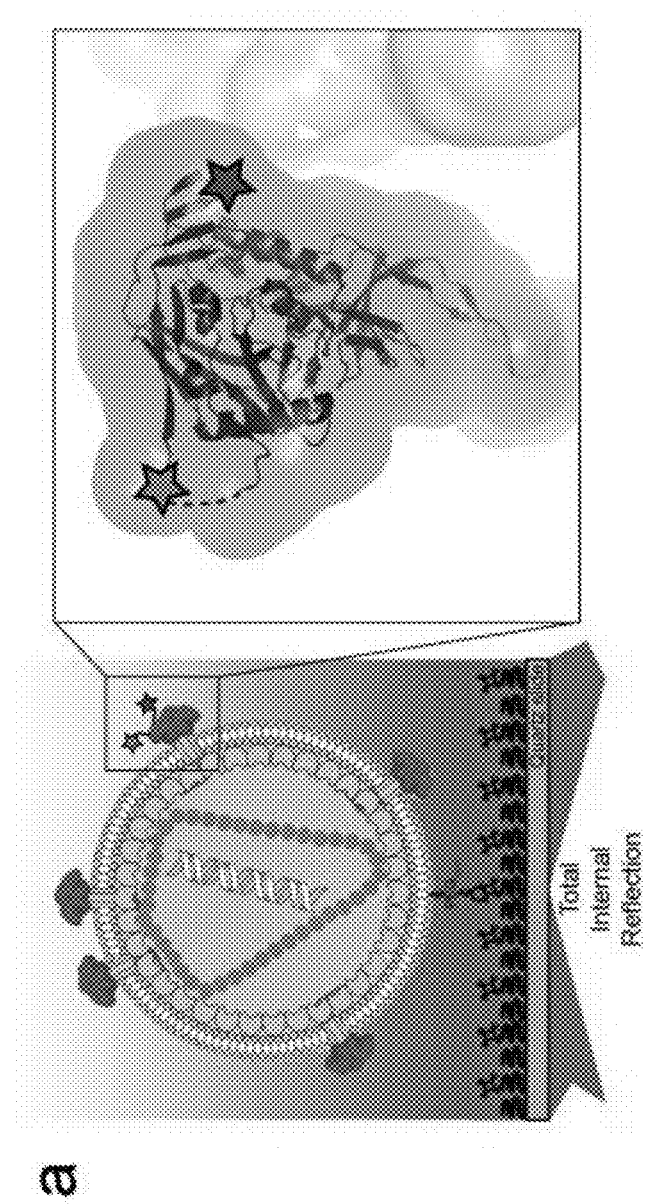
Figures 6B, 6C:
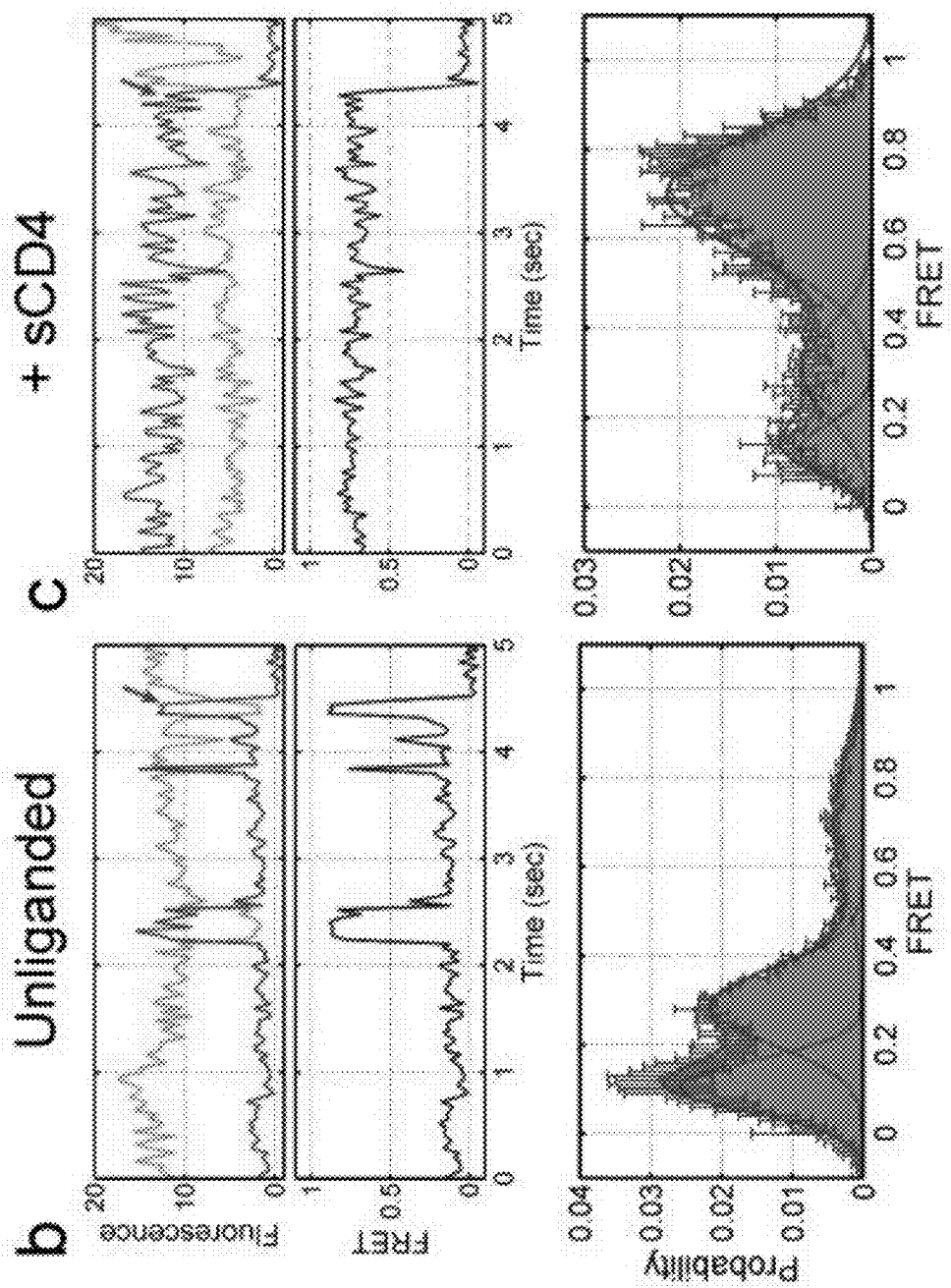

HIV-1 virions containing a single dually-labelled Env molecule (V1-3-Q3(AlexaFluor647)/V4-2-A1(Cy3)) incorporated into native unlabelled Env trimers were surface-immobilized and imaged using total internal reflection fluorescence (TIRF) microscopy (FIG. 6a). The donor fluorophore within the Env spike on several hundred surface-bound viruses was excited by a laser. Donor and acceptor fluorescence emissions were recorded, and the resulting FRET values calculated and compiled into population histograms (FIG. 6b, see Methods). These data revealed that the unliganded HIV-1 Env trimer spontaneously transitions between at least three conformations identified by three distinct FRET states: low ($0.11\pm0.01$), intermediate ($0.29\pm0.01$), and high FRET ($0.71\pm0.01$) (FIG. 6b), consistent with inter-fluorophore distances of ~70 Å, 55 Å and 45 Å, respectively. The evident transitions between these states indicate that the unliganded trimeric HIV-1 Env on the surface of intact virions is intrinsically dynamic, and spontaneously samples minimally three conformations.

Matching FRET Observations with Functional States

Figures 6D, 6E:
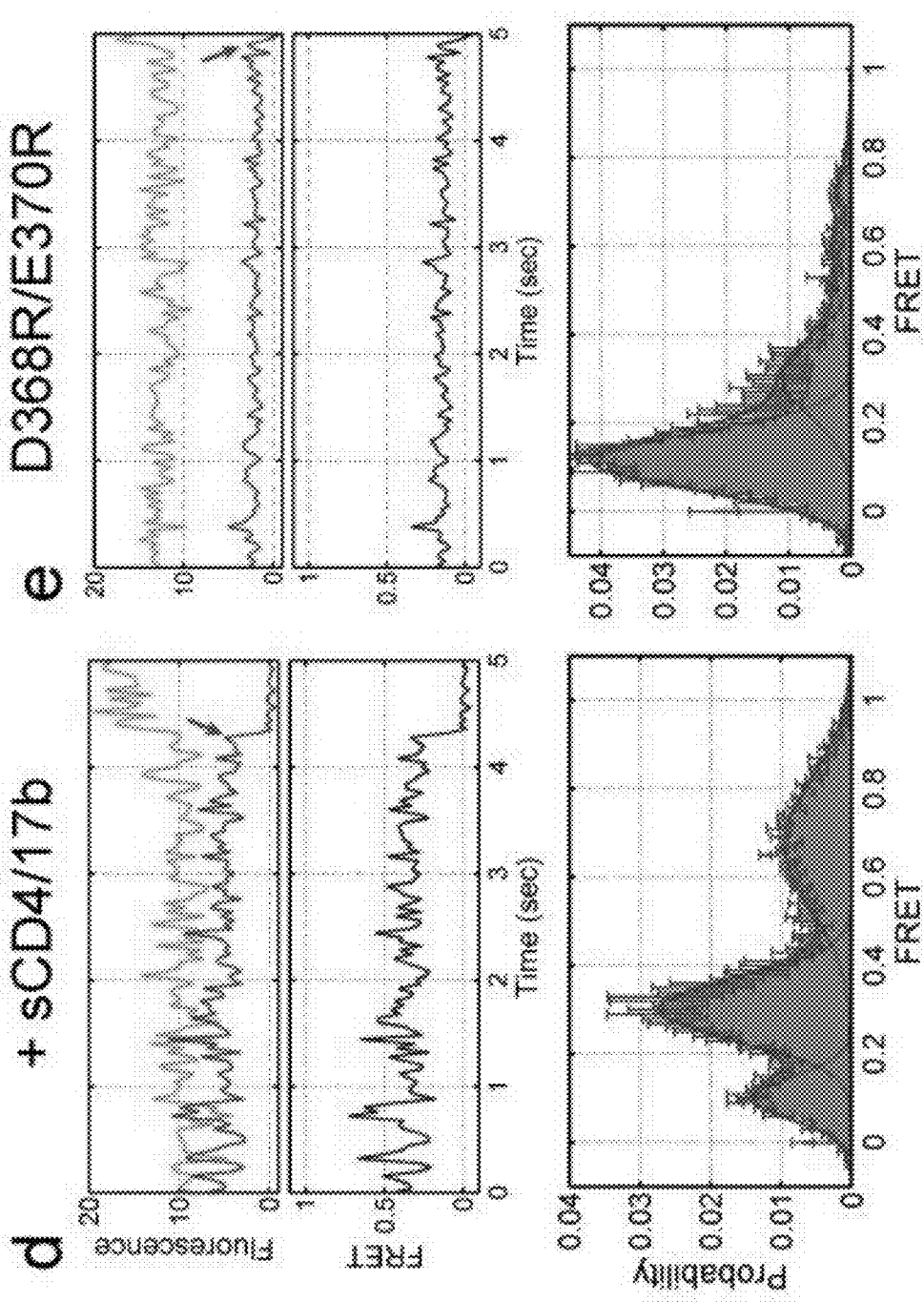

We next sought to identify the nature of the three conformational states by incubating HIV-1 Env with cognate ligands. First, the addition of sCD4 (D1D2 domains) to surface-bound HIV-1 at a concentration shown to be fully neutralizing enriched the subpopulation of molecules displaying stable high FRET (FIG. 6c). This observation is consistent with the high-FRET state corresponding to the CD4-bound conformation of gp120 within HIV-1 Env (Liu et al., *Nature* 455, no. 7209 (2008): 109-13). Because the high-FRET state is also observed in the absence of sCD4, this conformation is likely intrinsically accessible to the unliganded HIV-1 Env trimer. Next, we probed the effect of coreceptor binding on the conformational dynamics by incubating HIV-1 Env with the antigen-binding fragment (Fab) of the coreceptor-surrogate antibody 17b. In the presence of sCD4, this antibody binds to the coreceptor-binding site and is believed to promote a conformation of HIV-1 Env that resembles the coreceptor-bound state (Kwong et al., *Nature* 393, no. 6686 (1998): 648-59; Liu et al., *Nature* 455, no. 7209 (2008): 109-13; Sullivan et al., *J Virol* 72, no. 6 (1998): 4694-703). Incubation of the virus with sCD4 and 17b promoted formation of the intermediate-FRET state (FIG. 6d). The considerable occupancy in the intermediate-FRET state observed in the unliganded case suggests that HIV-1 Env is also intrinsically capable of adopting the conformation stabilized by the coreceptor. Interestingly, 17b alone failed to stabilize the intermediate-FRET state. Stabilization of the intermediate-FRET state required the additional presence of sCD4, consistent with the observation that the 17b antibody recognizes a CD4-induced conformation (Sullivan et al., *J Virol* 72, no. 6 (1998): 4694-703; Kwong et al., *Nature* 393, no. 6686 (1998): 648-59; Liu et al., *Nature* 455, no. 7209 (2008): 109-13). Similar dynamic data on the unliganded HIV-1 Env were obtained with the second dually labelled HIV-1 Env (V1-3-A1/V4-2-A1), which contained an alternative peptide insertion in V1, thereby confirming that our results are not dependent on the labelling peptides and dyes.

Thus, the high- and intermediate-FRET states sampled by the unliganded HIV-1 Env resemble the CD4 and CD4/17b-stabilized states, respectively. This suggests that the low- FRET state represents the native ground state of HIV-1 Env. In contrast to the CD4- and CD4/17b-bound conformations, no atomic-level structure exists for the ground state of the full-length gp120 domain of HIV-1 Env (Kwong et al., Nature 393, no. 6686 (1998): 648-59; Pancera et al., Proc Natl Acad Sci USA 107, no. 3 (2010): 1166-71). We therefore sought to identify conditions that stabilize the low-FRET state. HIV-1 Env carrying the mutations D368R and E370R in the CD4 binding pocket of gp120 (Olshevsky et al., J Virol 64, no. 12 (1990): 5701-7) displayed stabilization of the low-FRET state, and decreased occupancy in the intermediate- and high-FRET states (FIG. 6e). The D368R and E370R mutations are known to reduce CD4 binding to HIV-1 Env by more than 300 fold each. Indeed, minimal changes were observed in the FRET distribution in the presence of sCD4. D368R destroys the backbone hydrogen-bonding of D368 to the bridging sheet (Kwong et al., Nature 393, no. 6686 (1998): 648-59). Thus, our data are consistent with a model in which these mutations destabilize the CD4-bound conformation, thereby favouring the ground state.

CD4-Induced Conformation is a Preferred Intermediate

Figures 7A, 7B, 7C:
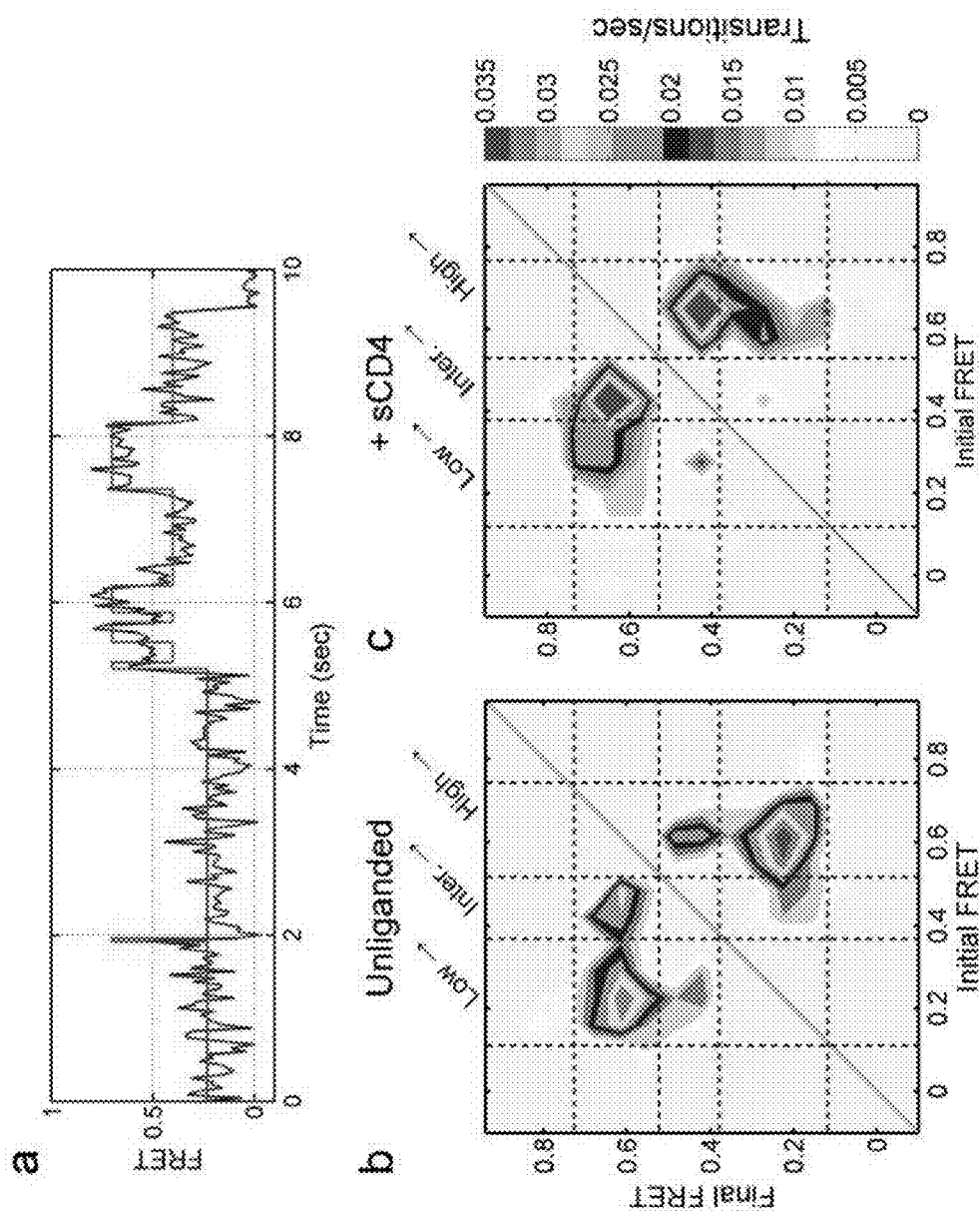

We next investigated the sequence of conformation changes of the unliganded HIV-1 Env through the application of hidden Markov modelling. The smFRET trajectories were first fit to a three-state Markov chain model (FIG. 7a). Transition-density plots (TDPs) (McKinney et al., Biophys J 91, no. 5 (2006): 1941-51), which display the relative frequencies of the observed transitions, were then formed from the idealized trajectories (FIG. 7b). The TDP for the unliganded Env indicated that the most frequent transitions occurred between the low- and high-FRET states. The second most frequent transitions occurred between the high- and intermediate-FRET states. Rarely were transitions seen between the low- and intermediate-FRET states. Thus, the TDP for the unliganded HIV-1 Env reveals a low probability for transition from the ground state (low FRET) to the 17b-stabilized state (intermediate FRET). Rather, the HIV-1 Env trimer must first transition from the ground state to the CD4-stabilized state prior to transition to the 17b-stabilized conformation. Since the 17b-stabilized state is the conformation closest to the activated coreceptor-bound state of HIV-1 Env, this analysis suggests that HIV-1 Env requires CD4 to efficiently reach the activated state. We tested this model by performing the same analysis for the sCD4-bound Env. In the presence of sCD4 the most frequent transitions were observed between high and intermediate FRET (FIG. 7c). Again, virtually no transitions were observed between low and intermediate FRET. Thus, CD4 promotes transitions between the high and intermediate FRET state thereby preparing HIV-1 Env for coreceptor binding and activation.

Figures 7D, 7E, 7F, 7G:
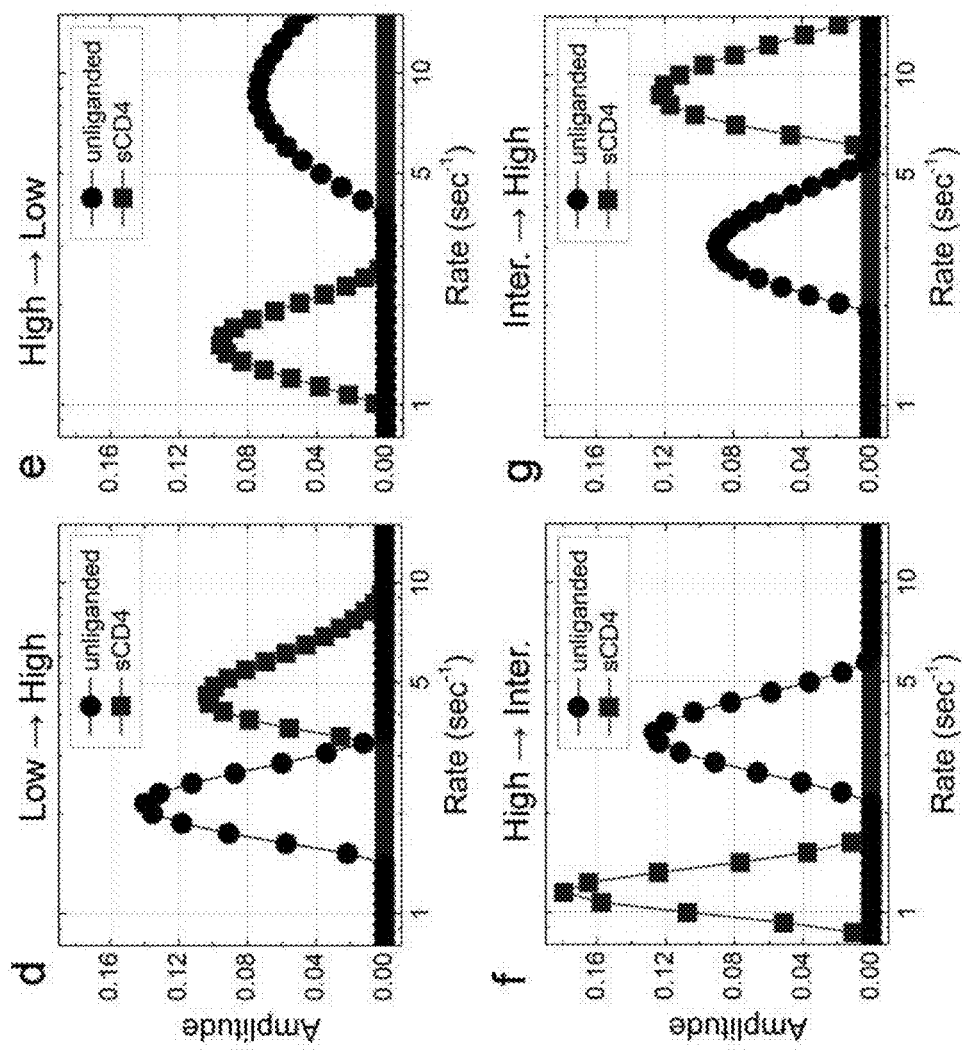
Figure 8A:
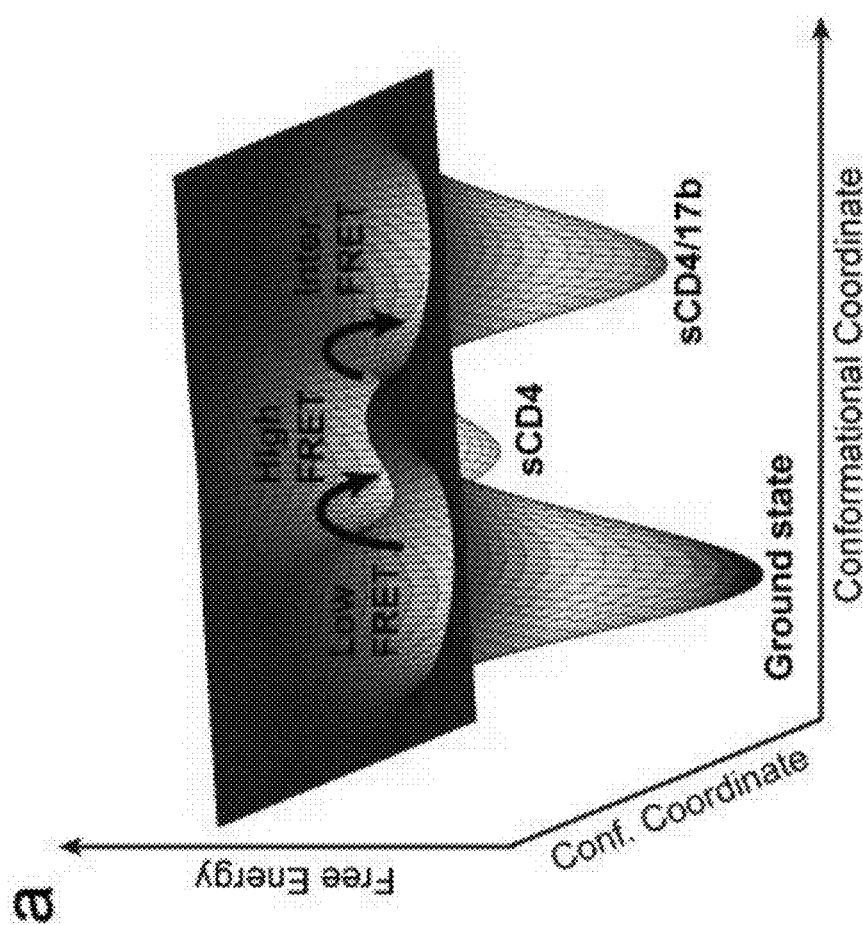
Figure 8B:
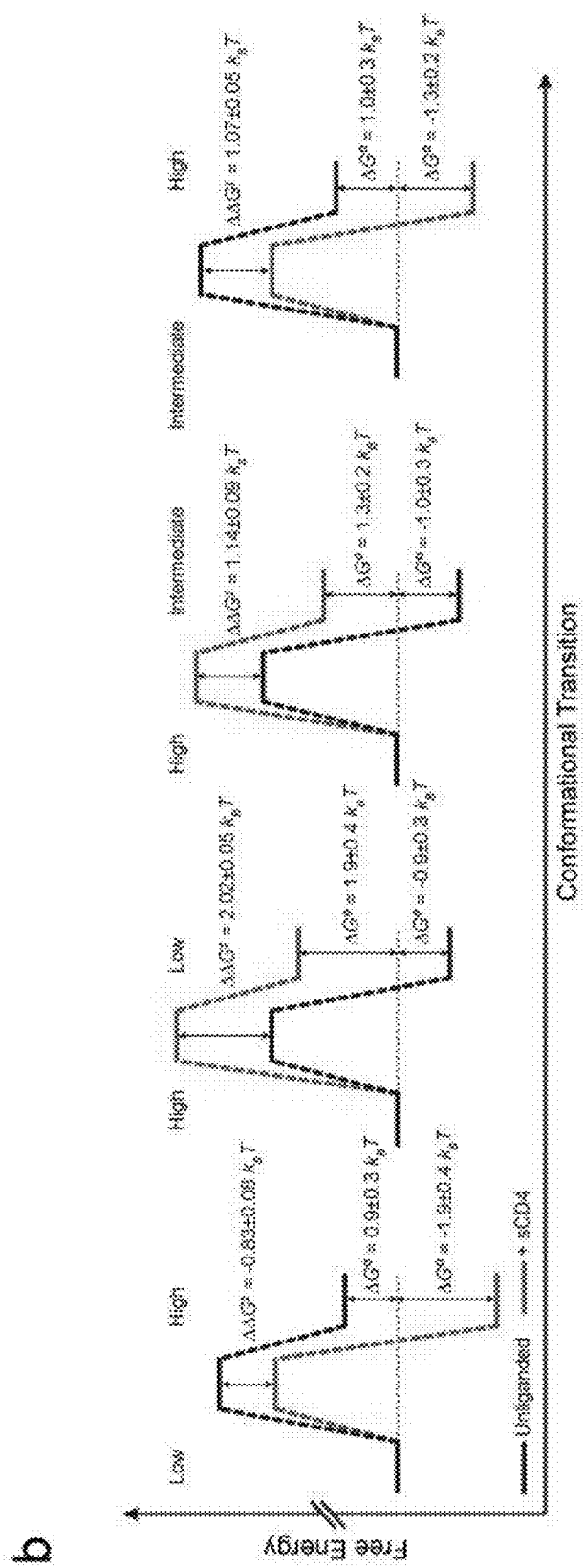

The observation that the activated conformation of Env is preferentially obtained by way of the high-FRET CD4-stabilized state suggests that the low- and intermediate-FRET states are separated by a high activation energy barrier (FIG. 8a). CD4 binding thus allows HIV-1 Env to reach the activated state, which is vulnerable to neutralization by antibodies and to premature inactivation. Further thermodynamic and kinetic analyses of the smFRET trajectories provide support for this model. The relative free energies of the conformational states were estimated from the occupancies in the observed FRET states (FIG. 6). This analysis revealed that CD4 binding reduced the free energy of the high-FRET state (FIG. 8b). In addition, the rates of transitions between the observed FRET states were determined by fitting histograms of dwell times to exponential functions using the maximum entropy method (FIG. 7d-g). The changes in activation energies upon CD4 binding were thus estimated from the transition rates (FIG. 8b). This indicated that CD4 binding decreased the activation energy for both transitions into the high-FRET state, from the low-FRET and from the intermediates-FRET states (FIGS. 7d, g, and 8b). CD4 binding also increased the activation energy for transitions out of the high-FRET state (FIGS. 7e, f and 8b). Therefore, the combined effects of the stabilized high-FRET state, the decreased energy barriers for transitions into that state, and the increased energy barriers for transitions out of that state, explain the observed long-lived nature of the CD4-bound conformation (FIG. 6c).

Integration of smFRET with Structural Models

The extensive structural characterization of the complete HIV-1 Env trimer by cryo-electron microscopy (cryo-EM) and tomography (cryo-ET), and of various forms of gp120 by X-ray crystallography provided an opportunity to place our smFRET observations into a structural context. We therefore generated models of the unliganded Env spike in the ground state, the CD4-stabilized state, and the CD4/17b-stabilized state, to provide three-dimensional depictions of the conformations observed via smFRET. Electron microscopy reconstructions of these three states of HIV-1 Env on the surface of virions have been published in the context of the BAL isolate (HIV-$1_{BAL}$) by Subramaniam and colleagues at a resolution of ~20 Å (Liu et al., Nature 455, no. 7209 (2008): 109-13; Tran et al., PLoS Pathog 8, no. 7 (2012): e1002797), with the ground-state structure determined in its unliganded form as well as in complex with the neutralizing antibodies VRC01 and VRC03 (Tran et al., PLoS Pathog 8, no. 7 (2012): e1002797). The conditions used to obtain cryo-ET structures for the CD4- and CD4/17b bound structure were equivalent to our smFRET conditions (Liu et al., Nature 455, no. 7209 (2008): 109-13) Importantly, while the functional state of gp120 is substantially different in these structures, the outer domain of gp120 appears to retain the same structure in both ground state and CD4-bound conformations (Chen et al., Structure 13, no. 2 (2005): 197-211; Pancera et al., Proc Natl Acad Sci USA 107, no. 3 (2010): 1166-71; Kwon et al., Proc Natl Acad Sci USA 109, no. 15 (2012): 5663-8; Guttman et al., J Virol 86, no. 16 (2012): 8750-64). This indicates that movement of the variable loops must critically contribute to the observed changes in FRET.

Because the outer domain of gp120 is too small to place accurately at ~20 Å resolution, we used the atomic-level structures of the VRC01 or VRC03 Fabs bound to gp120 to position the outer domain of gp120 in electron density maps of VRC01- or VRC03-bound HIV-$1_{BAL}$ Env spikes. We computationally excised density corresponding to the bound Fabs, and fit the resulting maps to the unliganded HIV-$1_{BAL}$ spikes to obtain an unliganded position for the gp120 outer domain in the unliganded state.

To correlate with the conformational changes observed via smFRET, we next sought to obtain structural models for the unliganded spike in CD4-stabilized and CD4/17b-stabilized conformations. To this end, we fit atomic level models of gp120 bound to sCD4, or of ternary complexes of gp120 bound to sCD4 and 17b into corresponding maps of the HIV-$1_{BAL}$ spike. Electron density corresponding to the bound ligands facilitated accurate positioning of the gp120 outer domain in each case. Five different structures of the gp120 outer domain bound to sCD4 were fit into the sCD4-bound electron density map and an average position of the fitted structures was determined Each of the five fitted structures displayed an average Cα RMSD of 3.5 Å from the calculated average fit. Likewise, two structures of the gp120 outer domain bound to sCD4 and 17b were fit into the corresponding electron density with an average Cα RMSD of 0.6 Å from the average position. These fitted structures yielded atomic resolution models for ligand-oriented outer domains in the sCD4-bound and sCD4/17b-bound electron density maps. In the final step the fitted complexes were then used to computationally excise sCD4 and 17b from these electron density maps. Overall, these structural models, as well as those with VRC01 and VRC03, allowed us to define unliganded electron density maps with positioned gp120 outer domain in ground state, CD4-stabilized, and CD4/17b-stabilized conformations.

The gp120 Conformational Machine

To compare the motions of the Env spike predicted by our structural models to those experimentally observed with smFRET, we aligned electron density maps corresponding to ground state, CD4-stabilized, and CD4/17b-stabilized conformations by maximizing map correlations. In the transition from the ground state to the CD4-stabilized conformation, electron density at the tip of the spike appears to separate and move away from the trimer axis. This electron density protrudes in the CD4-stabilized conformation in the same general region outlined by the mobile V1/V2 domains in PG9-defined negative stained gp120 maps (McLellan et al., *Nature* 480, no. 7377 (2011): 336-43). The volume of the protrusion also fit well with the expected volume for the protein component of V1/V2, thus allowing us to assign this prominent protrusion to the V1/V2 region. The movement from the membrane-distal cap region to the axial position agreed with FRET measurements that indicate V1/V2-V4 distance in the CD4-bound state to decrease from the ground state. Large scale changes in spike structure did not appear to occur in the transition from the CD4-stabilized to the CD4/17b-stabilized conformation. Notably however, the V1/V2-V4 distance did appear to lengthen, in agreement with smFRET measurements.

In addition to motions of the V1/V2 loop, our structural models provide insight into the movement of the center-of-mass (COM) of gp120 outer domain. For the ground state to CD4-stabilized conformation, these indicate movement (11±4 Å) in outer domain center-of-mass towards the trimer axis and away from the viral membrane. A 57±11° rotation aligns the α2-helix closer to the trimer axis, rotating from an orientation that would place the CD4 receptor perpendicular to the viral membrane, to one that is more axial. In transitioning from the CD4-bound conformation to the CD4/17b-bound conformation, a translation of 5±3 Å moves the outer domain center-of-mass away from the trimer axis, with a 30±8° rotation.

To assess the agreement between our structural models and the observed transitions in FRET, we determined the distances between the COM of the V1/V2 loop and the position of the V4 loop for all three structures. Because of the unknown and possibly intertwined packaging of the three V1/V2 loops at the tip of the unliganded Env trimer, we considered the distance from the COM of each of the three V1/V2 loops to a given V4 loop of a monomer. smFRET measurements and structural considerations suggest a model in which the V1/V2 loop of a monomer makes contact with the neighboring monomer in the counter-clockwise direction, consistent with previous results (Rusert et al., *J Exp Med* 208, no. 7 (2011): 1419-33). Structural modelling of the distances between V1/V2 and V4 loops in the ground state, CD4-stabilized conformation, and CD4/17b-stabilized conformation provided estimates of 86 Å, 70 Å, and 76 Å, respectively, with uncertainties of approximately 14 Å (the radius of a sphere encompassing V1/V2). These distances are in qualitative agreement with the larger FRET change observed for the transition from the ground state to the CD4-stabilized state, and the smaller change from the ground state to the CD4/17b-stabilized state.

Finally, we integrated the defined alterations in electron-density maps and position of gp120 outer domain with the timescale of the transitions indicated by the individual smFRET trajectories to provide the first real-time movie of spontaneous conformational changes undergone by the unliganded HIV-1 Env spike. This movie summarizes our findings which show unliganded HIV-1 Env to be conformationally dynamic and to intrinsically sample conformations required for function. Thus, models where CD4 "induces" conformational changes in gp120 to expose the co-receptor binding site may need to be revised. Our results indicate that gp120 is a molecular machine that intrinsically samples discrete conformational states. CD4 binding stabilizes a pre-existing conformation by remodelling the energy landscape of gp120 to favour a conformation that is an intermediate in the viral entry reaction. This suggests that the gp120 domain has characteristics that typify an enzyme, whose activity is regulated through ligand-induced modulation of intrinsically accessible conformations required for function (Munro et al., *Trends Biochem Sci* 34, no. 8 (2009): 390-400; Henzler-Wildman et al., *Nature* 450, no. 7172 (2007): 964-72).

smFRET Between HIV-1 Env and Receptor CD4.

Figure 9B:
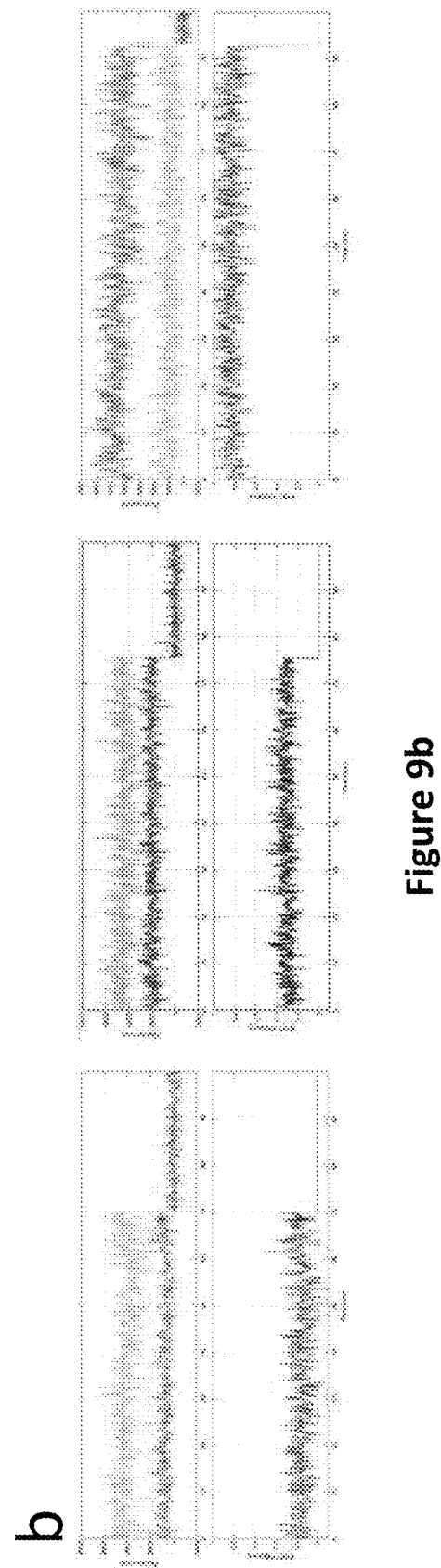

We also directly monitored the binding reaction of soluble CD4 (D1-D2) to HIV-1 Env. HIV-1 Env labeled with Cy3 at the LV4-2-A1 loop insertion was incubated with Cy5-labeled soluble CD4(C92) (FIG. 9A). Visual inspection revealed three subpopulations of traces each displaying a distinct FRET state: high-, intermediate-, or low-FRET states (0.85, 0.3, and 0.2, respectively) (FIG. 9B). Transitions between these states were never observed. Quantification of the traces for each of the three subpopulations revealed that they were observed with equal frequency (FIG. 9C). Consistent with this analysis, histograms of the observed FRET states were well fit by the sum of three Gaussians (FIG. 9C). The observed FRET values were approximately consistent with the modeled distances between CD4(C92-Cy5) bound at each of the three binding sites on the HIV-1 Env trimer, and the labeled gp120 (LV4-2-A1(Cy3)) (Kwong et al., *Nature* 393, 648-659; Liu et al., *Nature* 455, 109-113). That is, the asymmetric nature of CD4 binding to the HIV-1 Env trimer generates two closely related low-FRET states indicative of binding to the two unlabeled gp120 molecules within the trimer (FIG. 9D). The high-FRET state indicates CD4 binding to the labeled gp120 domain. Thus, these experiments indicate that soluble CD4 binds to all three gp120 molecules within the HIV-1 Env trimer. SmFRET is evidently capable of distinguishing the specific position of CD4 binding within the HIV-1 trimer. These data also demonstrate that the dye-labeled Env is not impaired in binding to CD4 as compared to the two wild-type molecules of the Env trimer. Moreover, this approach allows access to the study of cooperativity among the subunits of the trimer. These experiments document that we have established smFRET for the X4-tropic HIV-1 $Env_{NL4-3}$ and are extendible to R5-tropic primary isolate of HIV-1.

Three-Color smFRET—

HIV-1 Env can be dually labeled as in Example 1, and a ligand such as CD4 or 17b can be labeled with an additional dye, e.g., a Cy7 fluorophore, which is well-suited as an acceptor for FRET from Cy5. Three-color smFRET will allow monitoring of the conformational dynamics in gp120 in parallel with direct observation of ligand or inhibitor binding.

Example 3. smFRET Technologies for the Imaging of the R5-Tropic Isolates HIV-1$_{JR-FL}$, HIV-1$_{BAL}$ and HIV-1$_{KNH1144}$ The smFRET methodology described above for X4-tropic HIV$_{NL4-3}$ is applied to R5-tropic isolates HIV-1$_{JR-FL}$, HIV-1$_{BAL}$ and HIV-1$_{KNH1144}$. Labeling peptides such as A1 and Q3 tags can be inserted into the extendable variable loops LV1-V4 of gp120 for site-specific enzymatic labeling. Positions for such insertions can be selected based on structures of the variable loops solved by the Kwong group (McLellan et al. (2011) *Nature* 480, 336-343; Huang et al. (2005) *Science* 310, 1025-1028; Huang et al (2007) *Science* 317, 1930-1934), emerging structures of the HIV-1 Env trimer in the Sodroski and Subramaniam laboratories (White et al. (2010) *PLoS Pathog* 6, e1001249; Liu et al. (2008) *Nature* 455, 109-113), and previous insertions into variable loops of gp120 (Xiang et al. (2010) *J Virol* 84, 3147-3161; Ren et al. (2005) *J Virol* 79, 5616-5624; Laird et al. (2007) *J Virol* 81, 10838-10848; Leung et al. (2008) *Cell Host Microbe* 3, 285-292). Loops that are variable in sequence and length, are exposed and contain glycosylation sites, represent suitable sites for the insertion of, and replacement with, peptides for site-specific labeling.

Modified HIV Env variants (e.g., dually labeled) are selected based on minimally affected infectivity and an intact quaternary structure as determined by antibody neutralization assays. HIV-1$_{JR-FL}$ is resistant to PG9/PG16, which are broadly neutralizing antibodies that recognize the Env trimer interface. However, the single point mutation E168K renders HIV-1$_{JR-FL}$ sensitive to PG9/PG16 (Walker et al., *Science* 326, 285-289, 2009). Therefore, neutralization assays for HIV Env$_{JR-FL}$ variants can be performed in the E168K background. Well-behaved HIV-1 virions carrying only one dually labeled Env molecule among an excess of unlabeled Env are immobilized for TIRFM imaging. Image acquisition and data analysis are carried out as described for the X4-tropic HIV-1$_{NL4-3}$ above to reveal the number and occupancies of the observed FRET states. Hidden Markov modeling will be used to determine the rates of interconversion between distinct FRET states. Addition of the soluble receptor sCD4 (D1D2), sCD4 and antibody 17b, and the tyrosine-sulfated N-terminal fragment of CCR5 can provide insights into conformational trajectories within gp120 of HIV-1 Env that are associated with activation. Given that the Env trimer from all HIV isolates has the same function, it is expected that the same three FRET states and conformations identified with HIV-1$_{NL4-3}$ will be observed with other viral isolates, although the frequency at which these states are sampled, or the stability of the states, may vary.

smFRET for a representative clade C isolate such as ZM109, and the clade E isolate 93TH057 can also be established using the methodology disclosed herein. Image acquisition and FRET trace analysis are carried out as described for the X4-tropic HIV-1$_{NL4-3}$.

Example 4. Establishing smFRET Profiles of HIV-1 Agonists and Antagonists as Basis for Screening of New Inhibitors The establishment of smFRET for HIV-1 Env allows for a determination of the conformational consequences induced by small-molecule compounds that target the CD4 binding pocket in gp120. The X-ray crystal structure of gp120 bound to sCD4 revealed two highly conserved hot spots: (1) the Phe43$_{CD4}$ residue that reaches into the hydrophobic pocket within gp120; and (2) the Arg59$_{CD4}$ residue that establishes a salt bridge with Asp368$_{gp120}$. The NBD family of inhibitors appears to target the hydrophobic Phe43$_{CD4}$ binding pocket in gp120. It is generally believed that they behave like CD4 mimics as they promote CD4-independent entry into cells and feature a similar thermodynamic signature as CD4 with a highly favorable change in enthalpy, but unfavorable entropy. In contrast, inhibitors such as (+)-DMJ-I-228 that can also reach towards Asp368$_{gp120}$ no longer promote CD4-independent entry into cells, and exhibit a much-reduced entropic penalty. As such, rational design and synthesis allowed a transformation of the NBD family of agonists into antagonists. Here, smFRET can be applied to directly test the conformational consequences of the transformation of agonists into antagonists.

HIV-1 virions carrying one single Env molecule dually labeled with Cy3 and Cy5 can be incubated with a 10-fold excess over the IC50 of a test inhibitor, or buffer control. Conformational events can be correlated with dose-response curves. The drug-bound virus is then be immobilized and monitored using TIRF microscopy, and the conformational processes within Env is analyzed as described above. The histogram of the observed FRET states directly addresses if the test inhibitor acts as CD4 mimetics based on the extent to which the CD4-stabilized conformation is formed.

Particular attention is given to the frequency and temperature dependence of conformational transitions, which permits the determination of energy barriers between individual conformational changes. In particular, JRC-II-191 is known to inactivate HIV-1 Env, and therefore indicates a shorter lifetime in the CD4-stabilized conformation before transition to an inactivated conformation. Moreover, the application of three-color smFRET, whereby the ligand carries a third dye such as Cy7, allows a direct temporal correlation between ligand binding and the conformational consequences in gp120.

In contrast to CD4 mimetics, JRC-II-11, JRC-II-192, and DMJ-I-228 do not enhance entry into cells lacking CD4 and are therefore believed to act as antagonists. SmFRET HIV Env in the presence of these inhibitors can reveal the conformational events underlying their inhibitory activities, whether they trap the molecule in its pre-activated state or divert the molecule into conformations that are off-pathway for viral entry.

Conformational Trajectories Underlying the Conversion of HIV-1 Env Agonists (CD4 Mimetics) into Antagonists.

We determined the conformational consequences of the agonists NBD-556 and JRC-II-191 as well as the antagonist (+)-DMJ-I-228 and compared them to the unliganded and sCD4 bound HIV-1 Env$_{NL4-3}$ (FIG. 10). All inhibitors were tested at concentrations 10-100-fold above the K$_d$ (100 µM). Interestingly, these experiments demonstrated that that NBD-556 and JRC-II-191 are clear agonists as they activate HIV-1 Env (FIG. 10c, d). However, surprisingly, rather than inducing conformational changes that resemble that of sCD4 (FIG. 10b), they induced an intermediate-FRET state resembling the state stabilized by CD4 and co-receptor surrogate 17b. These findings suggest that small molecules that bind in the Phe43 cavity influence Env conformation differently than sCD4. CD4 may optimally stabilize a structural intermediate that prepares HIV-1 Env for efficient co-receptor binding. The ability of these agonists to induce the activated (CD4/17b stabilized) conformation may explain their tendency to lead to inactivation of HIV-1 Env. We also found that the antagonist (+)-DMJ-I-228 minimally changed the FRET distribution of the unliganded Env, despite its ability to block sCD4 binding (FIG. 10e, f). These data are in agreement with thermodynamic characterizations that found a minimal entropic contribution for (+)-DMJ-I-228 binding. While these data reveal surprising new insights, they are consistent with the thermodynamic hypothesis that an agonist to antagonist conversion correlates with reduced entropic penalties due to reduced allosteric signaling.

Additional inhibitors can be systematically tested along the agonist to antagonist conversion spectrum. These inhibitors will include TS-II-224, NBD-556, JRC-II-191, MAE-II-35, MAE-116, MAE-II-167, AS-I-215, AS-II-142, AS-II-203, DMJ-II-38, (+)-DMJ-I-228, and (1R,2R)-DMJ-II-121. These inhibitors have been extensively characterized thermodynamically; the degree of CD4 dependence and independence has been tested in cell-based assays; and the binding of some of these inhibitors to the monomeric gp120 core has been characterized structurally.

The application of three-color FRET, whereby the ligand carries a third dye such as Cy7, allows for a direct temporal correlation between inhibitor binding and the conformational consequences in gp120. Towards this end, agonists and antagonists that carry Cy7 can be synthesize. Three-color smFRET will reveal whether a test compound interacts with HIV-1 Env by a conformational capture or an induced fit mechanism.

Mechanism of Action for Peptide Triazoles.

We determine the conformational consequences in gp120 imposed by peptide triazole inhibitors. Peptide triazoles such as HNG-156 may represent proof of concept candidates for ligand-induced entrapment of HIV-1 Env in the preactivated conformation. HNG-156 prevents both the binding of soluble CD4 as well as 17b (McFadden et al. (2012) *Antimicrob Agents Chemother* 56, 1073-1080; Gopi et al. (2009) *J Mol Recognit* 22, 169-174). Having characterized the conformational consequences of CD4 and 17b binding to gp120, the peptide triazoles provide a particularly interesting means by which to compare the conformational trajectories of HIV-1 Env inactivation and with those of activation. SmFRET delineates the conformational trajectories and energy barriers. Our smFRET methodology allows for a comparison of the conformational entrapment facilitated by peptide triazoles with that of DMJ-I-228.

At nanomolar concentrations, the peptide triazole KR13 prevents the binding of CD4 and 17b (McFadden et al. (2012) *Antimicrob Agents Chemother* 56, 1073-1080; Gopi et al. (2009) *J Mol Recognit* 22, 169-174.). Interestingly, at micromolar concentration, KR13 can induce virolysis, gp120 shedding, and p24 release (Bastian et al. (2011) *ChemMedChem* 6, 1335-1339, 1318.). Virolysis induced by peptide triazoles is inhibited by T20 peptides, which indicates that gp41 is involved in this process.

Mechanism of Action for BMS Inhibitors.

BMS-806 and BMS-626529 inhibitors target HIV-1 Env and we can apply smFRET technologies to determine their conformational effects on HIV-1 Env. The synthesis of Cy7-inhibitor conjugates will again permit the direct temporal correlation between inhibitor binding and the conformational consequences in gp120. smFRET experiments will provide structural and temporal observations of the inactivated states of the Env, which are entrapped by these potent small-molecule inhibitors.

smFRET-Based Screening of New Inhibitors Targeting HIV-Env

Small-molecule inhibitor libraries can be screened to identify allosteric compounds that allosterically induce, trap or divert HIV-1 Env into specific conformations. Screening in the absence and presence of sCD4 also allows for the identification of competitive inhibitors that have little or no conformational effects on HIV-1 Env, yet block the induction of the CD-induced conformation.

What is claimed is:

1. A modified HIV gp120 protein comprising a first mutation in a first variable loop, wherein said first mutation comprises an insertion of at least one amino acid in said first variable loop and said at least one amino acid inserted in said first variable loop is labeled with a first fluorophore.

2. The modified HIV gp120 protein of claim 1, wherein said first variable loop is selected from the group consisting of V1, V2, V3, V4 and V5.

3. A modified HIV gp120 protein comprising a first mutation in a first variable loop, wherein said first mutation comprises an insertion of at least one amino acid in said first variable loop, and wherein said at least one amino acid inserted in said first variable loop is a first unnatural amino acid.

4. A modified HIV gp120 protein comprising a first variable loop, wherein a first peptide is inserted into said first variable loop, wherein said first peptide is selected from the group consisting of the S6 tag, the A1 tag, and the Q3 tag.

5. A modified HIV gp120 protein comprising a first mutation in a first variable loop, wherein said first mutation comprises an insertion of at least one amino acid in said first variable loop, and comprising a second mutation in a second variable loop, wherein said second mutation comprises an insertion of at least one amino acid in said second variable loop for labeling with a first fluorophore.

6. The modified HIV gp120 protein of claim 5, wherein the second variable loop is different from the first variable loop and is selected from the group consisting of V1, V2, V3, V4 and V5.

7. The modified HIV gp120 protein of claim 6, wherein the first and second variable loops are V1 and V4.

8. The modified HIV gp120 protein of claim 5, wherein said at least one amino acid inserted in said second variable loop is an unnatural amino acid.

9. The modified HIV gp120 protein of claim 5, wherein a peptide is inserted into said second variable loop.

10. The modified gp120 protein of claim 9, wherein the peptide is selected from the group consisting of the S6 tag, the A1 tag, and the Q3 tag.

11. An isolated HIV Env trimer, comprising the modified HIV gp120 according to claim 1.

12. An isolated HIV Env trimer comprising a modified HIV gp120, and further comprising an unmodified HIV gp120, wherein the modified HIV gp120 comprises a first mutation in a first variable loop, and wherein said first mutation comprises an insertion of at least one amino acid in said first variable loop, and wherein said at least one amino acid inserted in said first variable loop is labeled with a first fluorophore.

13. The isolated HIV Env trimer of claim 12, composed of two copies of the unmodified HIV gp120 and one copy of the modified HIV gp120.

14. The isolated HIV Env trimer of claim 13, wherein the at least one amino acid inserted is labeled with at least one fluorophore.

15. The isolated HIV Env trimer of claim 13, wherein said first mutation comprises a first peptide inserted in the first variable loop, and wherein the modified HIV gp120 further comprises a second mutation comprising a second peptide inserted in a second variable loop and the peptides are labeled with a first and second fluorophores, respectively.

16. An isolated HIV Env gp140 soluble trimer, comprising a copy of a modified gp140 and two copies of unmodified gp140, wherein said modified gp140 comprises an insertion of at least one amino acid in a first variable loop, and an insertion of at least one amino acid in a second variable loop.

17. The isolated HIV Env gp140 soluble trimer of claim 16, labeled with a first fluorophore at said at least one amino acid inserted in the first variable loop and a second fluorophore at said at least one amino acid inserted in the second variable loop.

18. An isolated HIV virion, comprising the HIV trimer of claim 13.

19. An isolated HIV virion, comprising the HIV trimer of claim 15.

20. An isolated HIV virion, comprising the soluble trimer of claim 16.

21. An isolated HIV virion, comprising the HIV trimer of claim 17.

22. The modified HIV gp120 protein of claim 5, wherein said at least one amino acid inserted in the first variable loop is labeled with a second flourophore, and said at least one amino acid inserted in the second variable loop is labeled with the first flourophore.

* * * * *